United States Patent [19]

Martin et al.

[11] Patent Number: 5,292,760
[45] Date of Patent: Mar. 8, 1994

[54] 4-HETEROARYL-1,3-BENZODIAZEPINES AND 2-SUBSTITUTED-α-(HETEROARYL)BENZENEETHANAMINES

[75] Inventors: Lawrence L. Martin, Lebanon; Joseph F. Payack, Somerset; Salvatore M. Brucato, Carteret, all of N.J.

[73] Assignee: Hoechst-Roussel Pharmaceuticals Inc., Somerville, N.J.

[21] Appl. No.: 872,215

[22] Filed: Apr. 22, 1992

Related U.S. Application Data

[63] Continuation of Ser. No. 632,556, Jan. 28, 1991, abandoned, which is a continuation of Ser. No. 331,429, Mar. 30, 1989, abandoned, which is a continuation-in-part of Ser. No. 275,804, Nov. 29, 1988, abandoned, which is a continuation-in-part of Ser. No. 129,820, Dec. 7, 1987, abandoned.

[51] Int. Cl.⁵ .................... C07D 33/20; C07D 213/38; A61K 31/44; A61K 31/38
[52] U.S. Cl. .................... 514/357; 514/438; 546/329; 546/334; 546/337; 548/202; 548/204; 548/205; 548/335.5; 548/375.1; 548/561; 549/74; 549/75; 549/77; 549/492; 549/493; 540/567
[58] Field of Search .................... 549/74, 75, 77; 546/337, 329, 334; 548/561; 514/357, 438

[56] References Cited

PUBLICATIONS

P. K. Kadaba, Drugs of the Future, 15, pp. 1013–1024, 1990.
J. B. Uney et al., Scrip Reports Neurodegeneration and Neuroprotection, "Molecular and Cellular Events Accompanying Nerve Cell Death", pp. 35–40, 1990.
SCRIP Reports, Neurodegeneration and Neuroprotection, M. V. Sonfroniew et al., "Experimental Models of Neuronal Degeneration and Alzheimer's Disease", pp. 10–16 (1990).
D. M. Barnes on Science, 235, 632 (1987).

*Primary Examiner*—Robert Gerstl
*Attorney, Agent, or Firm*—Elliott Korsen

[57] ABSTRACT

Novel 4,5-dihydro-4-heteroaryl-3H-1,3-benzodiazepines, intermediates, processes for the preparation thereof, and methods for treating depression, inhibiting convulsions and treating anxiety utilizing compounds and compositions thereof are disclosed.

72 Claims, No Drawings

4-HETEROARYL-1,3-BENZODIAZEPINES AND 2-SUBSTITUTED-α-(HETEROARYL)BENZENEE-THANAMINES

This is a continuation of application Ser. No. 632,556 filed Jan. 28, 1991, now abandoned which is a continuation of application Ser. No. 331,429 filed Mar. 30, 1989, now abandoned, which is a continuation-in-part of application Ser. No. 275,804 filed Nov. 29, 1988, now abandoned, which is a continuation-in-part of application Ser. No. 129,820 filed Dec. 7, 1987, now abandoned.

This invention relates to 4,5-dihydro-4-heteroaryl-3H-1,3-benzodiazepines. More particularly, this invention relates to 4,5-dihydro-4-heteroaryl-3H-1,3-benzodiazepines of the formula:

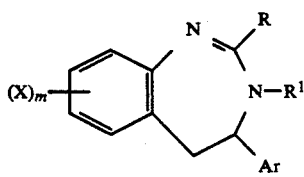

FORMULA I wherein Ar is a radical selected from the group consisting of

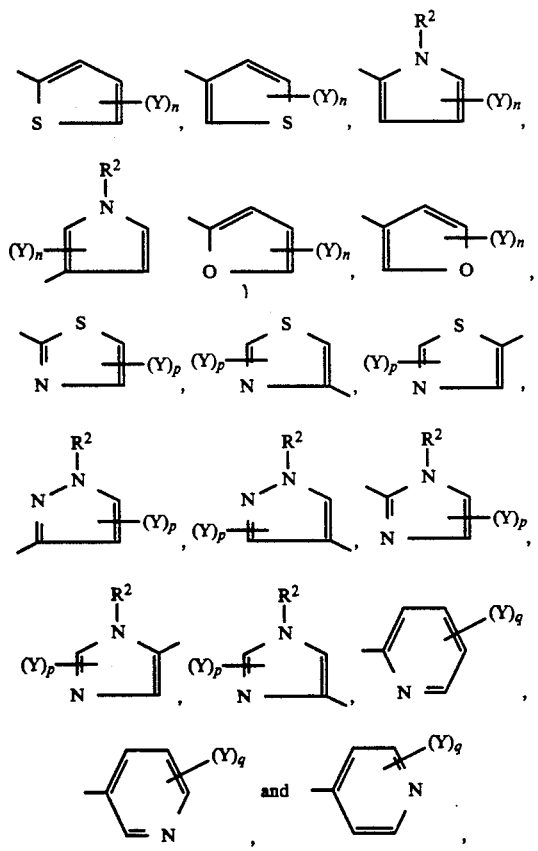

wherein $R^2$ is hydrogen, loweralkyl or loweralkanoyl, Y is selected from the group consisting of halogen, hydroxyl, loweralkyl, loweralkoxy, and trifluoromethyl, n is an integer having a value from 0 to 3 inclusive, p is an integer having a value of 0 or 1, and q is an integer having a value from 0 to 4 inclusive; X is selected from the group consisting of halogen, hydroxyl, nitro, loweralkyl, loweralkoxy, and trifluoromethyl; m is an integer having a value from 0 to 2 inclusive; R is selected from the group consisting of hydrogen, loweralkyl, aryl, aralkyl, cycloalkylloweralkyl, loweralkenyl, and loweralkynyl; and $R^1$ is selected from the group consisting of hydrogen, loweralkyl, and aralkyl, wherein for each value of m, n, p, or q each X or Y may be the same or different; the optical antipodes; geometrical isomers; or pharmaceutically acceptable acid addition salts thereof which are useful as antidepressants.

Preferred 4,5-dihydro-4-heteroaryl-3H-1,3-benzodiazepines of this invention are compounds of the formula:

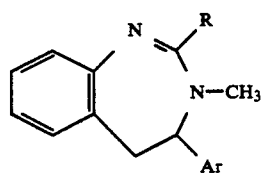

FORMULA II wherein Ar is selected from the group consisting of

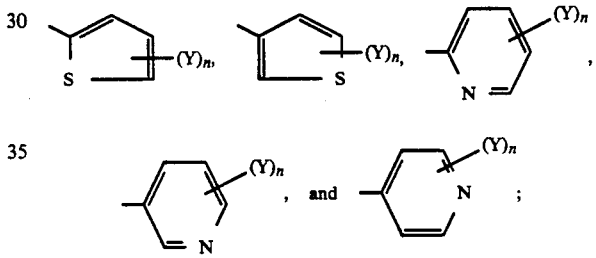

wherein Y is loweralkyl, most preferably methyl, n is an integer having a value of 0 or 1, and R is selected from the group consisting of hydrogen, loweralkyl, aralkyl, and aryl; the optical antipodes; geometrical isomers; or pharmaceutically acceptable acid addition salts thereof.

Subgeneric to the 4,5-dihydro-4-heteroaryl-3H-1,3-benzodiazepines of this invention are Formula I compounds wherein (a) Ar is

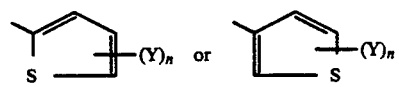

wherein Y and n are as previously described;

(b) Ar is

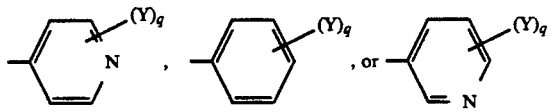

wherein Y and q are as previously described;

(c) Ar is

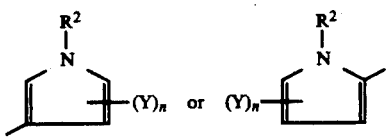

wherein R², Y and n are as previously described;
(d) Ar is

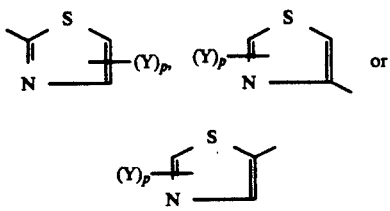

wherein Y and p are as previously described;
(e) Ar is

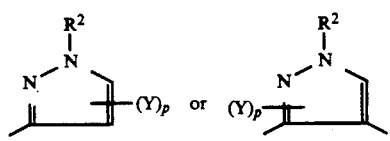

wherein R², Y and p are as previously described;
(f) Ar is

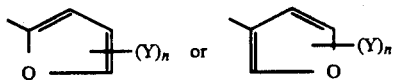

wherein Y and n are as previously described;
(g) Ar is

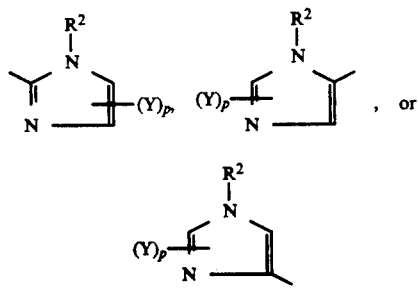

wherein R², Y and p are as previously described;
(h) R is hydrogen, loweralkyl, aryl, aralkyl, loweralkenyl or loweralkynyl;
(i) R is hydrogen, loweralkyl, aryl or aralkyl;
(j) R¹ is hydrogen;
(k) R¹ is loweralkyl, or aralkyl
(l) R² is hydrogen or loweralkyl;
(m) n is zero or 1;
(n) m is zero or 1;
(o) p is zero;
(p) q is zero or 1;
(q) X is loweralkyl;
(r) X is hydroxyl or loweralkoxy;
(s) X is halogen or trifluoromethyl;
(t) X is nitro;
(u) Y is hydroxyl or loweralkoxy;
(v) Y is loweralkyl;
(w) Y is halogen or trifluoromethyl; and
(x) Y is loweralkyl or chlorine.

In another embodiment this invention relates to compounds of the formula

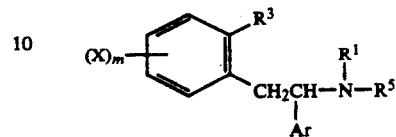

FORMULA III wherein Ar is selected from the group consisting of

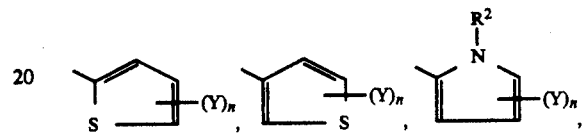

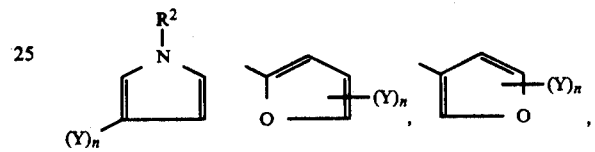

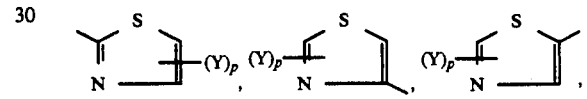

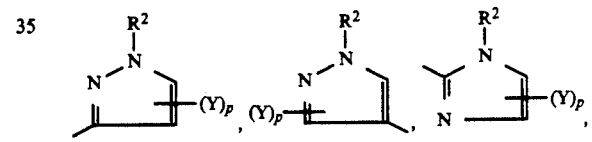

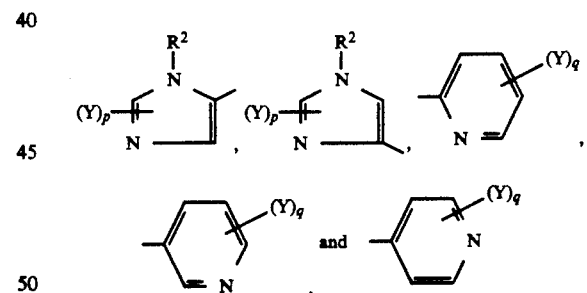

and wherein R² is hydrogen, loweralkyl or loweralkanoyl, Y is selected from the group consisting of halogen, hydroxyl, loweralkyl, loweralkoxy and trifluoromethyl, n is an integer having a value from 0 to 3 inclusive, p is an integer having a value of 0 or 1, and q is an integer having a value from 0 to 4 inclusive; X is selected from the group consisting of halogen, hydroxyl, nitro, loweralkyl, loweralkoxy, and trifluoromethyl; m is an integer having a value from 0 to 3 inclusive; R¹ is selected from the group consisting of hydrogen, loweralkyl, and aralkyl; R³ is hydroxy, loweralkoxy, amino, loweralkylamino, diloweralkylamino, nitro, or NR⁶C(O)R⁴ wherein R⁴ and R⁶ are independently hydrogen or loweralkyl; and R⁵ is hydrogen, loweralkyl or C(O)R⁷ wherein R⁷ is hydrogen or loweralkyl, wherein for each value of m, n, p or q, each X or Y may be the same or different; the geometrical isomers, optical antipodes or pharmaceutically acceptable acid addition salts thereof.

The Formula III compounds of this invention, are useful as anticonvulsants, neuroprotective and anxiolytic agents. Additionally, several of these Formula III compounds have utility as intermediates in the synthesis of the 4-heteroaryl-1,3-benzodiazepines of this invention. Subgeneric to the Formula III compounds of this invention are those compounds wherein (aa) $R^1$ is hydrogen;
(bb) $R^1$ is loweralkyl;
(cc) $R^1$ is aralkyl;
(dd) $R^3$ is amino;
(ee) $R^3$ is loweralkylamino;
(ff) $R^3$ is diloweralkylamino;
(gg) $R^3$ is $NR^6C(O)R^4$ wherein $R^4$ and $R^6$ are independently hydrogen or loweralkyl;
(hh) $R^3$ is hydroxy;
(ii) $R^3$ is loweralkoxy;
(jj) $R^5$ is hydrogen;
(kk) $R^5$ is $-C(O)R^7$ wherein $R^7$ is hydrogen or loweralkyl,
(ll) $R^5$ is loweralkyl;
(mm) Ar is selected from the group consisting of

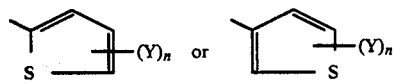

wherein n is an integer having a value of 0 or 1 and Y is loweralkyl, most preferably methyl.

(nn) Ar is

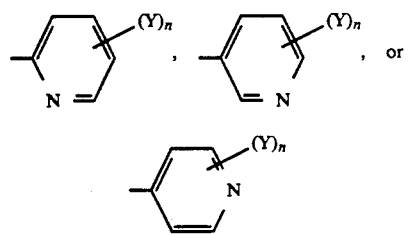

wherein n is an integer having a value of 0 or 1 and Y is loweralkyl, most preferably methyl.

(oo) Ar is

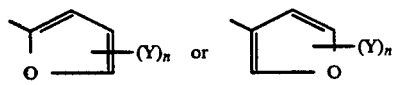

wherein n is an integer having a value of 0 or 1 and Y is loweralkyl, most preferably methyl.

A class of preferred 2-substituted-α-(heteroaryl)benzeethanamines of this invention is represented by the formula:

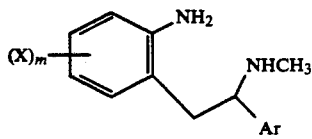

FORMULA IV wherein X is halogen, preferably bromine or chlorine, m is zero or 1, and Ar is

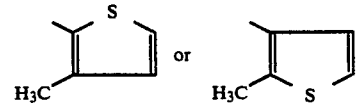

As used throughout the specification and appended claims, the term "loweralkyl" shall mean a straight or branched chain hydrocarbon group containing no unsaturation and having from 1 to 5 carbon atoms such as methyl, ethyl, 1-propyl, 2-propyl, 1-butyl, 1-pentyl, 2-pentyl, and the like. The term "cycloalkyl" shall mean a saturated hydrocarbon group possessing at least one carbocyclic ring and having from 3 to 7 carbon atoms such as cyclopropyl, cyclobutyl, cyclopentyl, cyclohexyl, cycloheptyl, and the like. The term "loweralkoxy" shall mean a monovalent substituent which consists of a loweralkyl group linked through an ether oxygen and having its free valence bond from the ether oxygen, such as methoxy, ethoxy, isopropoxy, t-butoxy, pentoxy, and the like. The term "aryl" shall mean phenyl or phenyl substituted with one or more chloro, bromo, fluoro, loweralkyl, methoxy, hydroxy, or trifluoromethyl groups. The term "aralkyl" refers to a radical formed by attachment of a loweralkyl function having up to 4 carbon atoms, inclusive to an aryl moiety. The term "alkanoyl" shall mean the residue of an alkyl carboxylic acid (alkanoic acid) having from 1 to 5 carbon atoms formed by the removal of the hydroxy group of the carboxylic acid moiety. Examples of alkanoyl groups include formyl, acetyl, propionyl, butyryl, pentanoyl and the like. The term "loweralkenyl" shall mean a saturated hydrocarbon group of 1 to 5 carbon atoms having one or more carbon-carbon double bonds, and the term "alkynyl" shall mean a hydrocarbon group of 1 to 5 carbon atoms having one or more carbon-carbon triple bonds.

As shown by Reaction Scheme A, Formula III compounds wherein $R^3$ is amino, $R^5$ is hydrogen and $R^1$ is loweralkyl or aralkyl are produced by reacting a N-(2-methylphenyl)-2,2-dimethylpropanamide 1, via the corresponding dilithium adduct 2, with a heteroaryl carboxaldehyde imine 3 to produce a heteroaryl-substituted intermediate 4, hydrolysis of which yields the corresponding diamine 5.

N-(2-methylphenyl)-2,2-dimethylpropanamide 1 can be synthesized by the reaction of o-toluidine and trimethylacetyl chloride as described in U.S. Pat. No. 4,374,067 to Lee et al., assigned to Hoechst-Roussel Pharmaceuticals, Inc. The reaction of primary aliphatic or aromatic amines with heteroaryl carboxaldehydes to yield heteroaryl carboxaldehyde imines is well known in the art and is analogous to the reaction of aromatic aldehydes and primary amines described, for example, in G. Hilgetag and A. Martini, Preparative Organic Chemistry, John Wiley & Sons, Inc., New York, 1972, pp. 504-409.

Production of the heteroaryl-substituted intermediate 4 is conveniently accomplished by first treating N-(2-methylphenyl)-2,2-dimethylpropanamide 1 with an organolithium compound (e.g. tert-butyllithium, sec-butyllithium, n-butyllithium, and the like; n-butyllithium being preferred) and thereafter converting the resultant dilithium adduct 2 to the heteroaryl-substituted intermediate 4 by reaction with the heteroaryl carboxaldehyde imine 3. In general, the reaction is conducted in the presence of an inert organic solvent without isolation of the intermediate dilithium adduct. Among the suitable solvents for the reaction there may be mentioned ethereal solvents, hydrocarbons, and the like, and mixtures thereof. Representative of such solvents are diethyl ether, dioxane, 1,2-dimethoxyethane, tetrahydrofuran, hexane, cyclohexane, benzene, toluene, xylene, and the like. Tetrahydrofuran, toluene, and mixtures thereof with hexane (commonly present as a solvent for the organolithium compound) are preferred. The reaction is ordinarily conducted at temperatures of from about −70° C. to about 30° C., with temperatures of about −10° C. to about 0° C. being preferred. Typically, the amount of organolithium compound reacted is up to about 10% in excess of the 2 molar equivalents required for the reaction. Owing to the reactivity of the organolithium compound, it is recommended that the reaction be conducted under anhydrous conditions.

Hydrolysis of the heteroaryl substituted intermediate 4 to the corresponding diamine 5 is conveniently accomplished in the presence of an aqueous solvent by an appropriate mineral acid (e.g. hydrochloric acid, hydrobromic acid, sulfuric acid and the like, 6N hydrochloric acid being preferred) under reflux conditions. Desirably the hydrolysis is conducted under an inert atmosphere to avoid undesirable side reactions.

As further illustrated in Reaction Scheme A, Formula III compounds wherein $R^3$ is amino or —NHC(O)$R^4$, and $R^5$ is —C(O)$R^7$ can be produced by treating a diamine 5 with a suitable alkanoic acid anhydride. (e.g. formic acid anhydride, acetic acid anhydride, propionic acid anhydride, butyric acid anhydride, pentanoic acid anhydride and the like). The acylation is generally conducted at temperatures of from about −30° C. to about 20° C., preferably from about 0° C. to about 10° C., in the presence of a suitable inert organic solvent. Suitable solvents include non-nucleophilic amines such as, for example, pyridine, lutidine, collidine, trimethyl amine, and the like. Pyridine is preferred.

Reduction of the resultant carbonyl derivatives 5a and 5b affords Formula III compounds 6a and 6b wherein $R^3$ is amino or loweralkylamino, and $R^5$ is hydrogen or loweralkyl. Reduction may be accomplished by any of several methods which are well known in the art. For example, treatment of formyl substituted derivatives 5a and 5b with a boron-tetrahydrofuran complex followed by hydrolysis with a mineral acid (e.g. concentrated hydrochloric acid).

Treatment of a formyl substituted derivative 5b with formaldehyde and succinimide followed by reduction of the resultant dioxo-pyrolidinyl substituted compound 6c, affords a derivative 6d wherein $R^3$ is methylamino. Hydrolysis of 6d with mineral acid or reduction provides compounds 6e where $R^5$ is hydrogen or loweralkyl.

Diazotization of derivatives 5b with nitrous acid and quenching into aqueous copper sulfate solution affords Formula III compounds 6f wherein $R^1$ is loweralkyl, $R^7$ is hydrogen or loweralkyl, and $R^{10}$ is hydrogen. Hydrolysis of carbonyl derivatives 6f with a mineral acid affords Formula III compounds 6g wherein $R^{10}$ is hydrogen. Alkylation of phenol 6f wherein $R^{10}$ is hydrogen by, for example, a dialkylsulfate $(R^{10}O)_2SO_2$ wherein $R^{10}$ is alkyl) yields an O-alkyl derivative 6f wherein $R^{10}$ is alkyl, which is hydrolyzed to amine 6 g wherein $R^{10}$ is alkyl.

It should be noted that, if desired, substitution of the phenyl ring of the Formula III compounds of this invention can be effected subsequent to formation of the diamine 5. For example, treatment of a phenyl-unsubstituted diamine 5 with a halosuccinimide (e.g. N-bromosuccinimide or N-chlorosuccinimide) provides the compound with one or more halide substitutes, X-.

Alternatively, as shown in Reaction Scheme B, Formula III compounds wherein $R^1$ and $R^5$ are hydrogen and $R^3$ is amino may be prepared by converting a heteroaryl-substituted 2-(2-nitrophenyl)acetophenone 7 to an oxime 8, acylating the oxime 8 with an alkanoic acid anhydride, and reducing the resultant oxime alkanoate 9 to a diamine 10.

The synthesis of heteroaryl-substituted 2-(2-nitrophenyl)acetophenones 7 is known in the art and is analogous to the synthesis of phenyl-substituted 2-(2-nitrophenyl)acetophenones described in greater detail in U.S. Pat. No. 4,459,231 incorporated herein by reference. Oxime conversion may be accomplished by any of several methods known in the art. A preferred method involves refluxing the 2-(2-nitrophenyl)acetophenone 7 in a mixture of ethyl alcohol, aqueous sodium acetate and hydroxylamine to provide the corresponding oxime 8. Alkanoic acid anhydrides suitable for acylation of the oxime 8 include formic acid anhydride, acetic acid anhydride, butyric acid anhydride, pentanoic acid anhydride, and the like. Acetic acid anhydride is preferred. The acylation is generally conducted at a temperature of from about 0° C. to about 100° C., preferably from about 0° C. to about 25° C., in the presence of pyridine. Reduction of the oxime alkanoate 9 may be accomplished by any of several methods known in the art, among which treatment with a boron-tetrahydrofuran complex followed by hydrolysis is preferred.

A diamine 10 is also prepared by condensing a 2-(2-nitrophenyl)acetophenone 7 with ammonia or an amine $R^9NH_2$ (wherein $R^9$ is loweralkyl) followed by reduction of the intermediate enamine/imine to provide a nitroamine 13 which is reduced to the desired diamine 10. The condensation is typically performed by treating an acetophenone 7 with ammonia or an amine $R^9NH_2$ wherein $R^9$ is as above in the presence of a water scavenger such as, for example, titanium tetrachloride in an aromatic solvent such as benzene, toluene, xylene, and the like, toluene being the preferred solvent. The reduction of the enamine/imine, so formed, is generally accomplished by contacting an enamine/imine, as the hydrohalide (e.g., a hydrochloride) with an alkali metal borohydride, i.e., a sodium, potassium, or lithium borohydride or cyanoborohydride in an alkanol such as methanol, ethanol, 2-propanol, and the like, sodium cyanoborohydride in methanol being the reducing system of choice. The reduction of a nitroamine 13 to a diamine 10 is conveniently carried out by treating a nitroamine 13 with a reducing metal such as, as an example, electrolytic iron, in the presence of a hydrohalic acid (e.g. hydrochloric acid) and an aqueous alkanol (e.g. aqueous ethanol). While the reaction temperatures of the aforementioned condensation and reduction reaction are not narrowly critical, the condensation-reduction sequence providing nitroamine 13 is preferably performed at room temperature, and the reduction step leading to diamine 10 is preferably carried out at the reflux temperature of the solvent system.

2-Dialkylaminobenzeneethanamines 14 wherein $R^1$ and $R^5$ are alkyl are prepared by reductive alkylation of 2-amino-N-alkanoylbenzeneethanamines 10 wherein $R^9$ is alkanoyl followed by hydrolysis of the amide function. For example, treatment of a benzeneethanamine 10 wherein $R^9$ is formyl with an alkanal $R^{10}CHO$ wherein R[10] is hydrogen or alkyl (e.g., formaldehyde) in the presence of an alkali metal cyanoborohydride (e.g., sodium or potassium borohydride) provides dialkylamine 14 wherein R[1], R[5], and R[9] are as above, which may be hydrolyzed by conventional methods, such as, in this instance, by aqueous alkali metal hydroxide (e.g., aqueous sodium or potassium hydroxide).

As shown in Reaction Scheme C, Formula III diamines 5 can be cyclized by reaction with a compound of the formula:

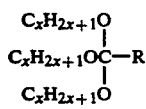

wherein R is hydrogen, loweralkyl, aralkyl or aryl, and x is 1 or 2, (e.g. trimethyl orthoformate, trimethyl orthoacetate, triethyl orthoacetate, trimethyl orthoacetate, triethyl orthoisopropionate, trimethyl orthoisobutyrate, trimethyl orthobenzoate, and the like) to provide Formula I 4,5-dihydro-4-heteroaryl-3H-1,3-benzodiazepines 12 wherein R is hydrogen, loweralkyl, alkyl or aryl. The cyclization is generally conducted in the presence of an appropriate acid catalyst (e.g. alkanoic or alkanolic acids such as, for example, glacial acetic acid, ethanolic hydrochloric acid, methanolic hydrochloric acid, and the like, glacial acetic acid being preferred, at a temperature of from about 25° C. to the reflux temperature of the reaction medium. Alternatively, the cyclization may be conducted in the presence of acetonitrile at a temperature of about 80° C. in the presence of an acid catalyst.

The Formula I compounds of this invention are useful as antidepressants by virtue of their ability to elicit an antidepressant response in mammals. Antidepressant activity is demonstrated in the tetrabenazine induced ptosis assay in mice [International Journal of Neuropharmacology, 8, 73 (1969)], a standard assay for antidepressant activity.

The intraperitoneal (i.p.) dosages at which the following compounds effect a 50% inhibition from the ptosis of tetrabenazine-induced depression in mice (ED$_{50}$) are:

TABLE 1

| Compound | Anti-Depressant Activity ED$_{50}$ (mg/kg, i.p.) |
|---|---|
| 4,5-Dihydro-2-ethyl-3-methyl-4-(2-thienyl)-3H-1,3-benzodiazepine hydrochloride | 4.7 |
| 4,5-Dihydro-2-ethyl-3-methyl-4-(3-thienyl)-3H-1,3-benzodiazepine hydrochloride | 8.7 |
| 4,5-Dihydro-2-ethyl-3-methyl-4-(3-methyl-2-thienyl)-3H-1,3-benzodiazepine hydrochloride monohydrate | 5.3 |
| 4,5-Dihydro-2-ethyl-3-methyl-4-(4-pyridinyl)-3H-1,3-benzodiazepine hemihydrate | 6.8 |
| 4,5-Dihydro-2,3-dimethyl-4-(2-methyl-5-thienyl)-3H-1,3-benzodiazepine hydrochloride | 12.2 |
| Doxepin (standard) | 3.8 |

Dosage levels which the 4-heteroaryl-1,3-benzodiazepines of this invention achieve an antidepressant response is subject to variation depending upon the particular compound employed. In general, antidepressant response may be elicited at effective oral, parenteral, or intravenous doses ranging from about 0.1 to about 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

The Formula III compounds of this invention are useful as anticonvulsants due to their anticonvulsant activity in mammals. Anticonvulsant activity is measured in the male mouse using the supramaximal electroshock (SES) assay described in Arch. Int. Pharmacodyn. 92: 97–107, 1952. Intraperitoneal doses of representative compounds of the invention and their ability to protect from the effect of SES is shown below in Table 2. ED$_{50}$ values, i.e., the doses at which, within 95% confidence intervals, 50% of the animals are protected are calculated by computerized probit analysis.

TABLE 2

| Compound | Anticonvulsant Activity ED$_{50}$ (mg/kg, i.p.) |
|---|---|
| 2-Amino-N-methyl-alpha-(3-methyl-2-thienyl)benzenethanamine | 4.6 |
| 2-Amino-N-methyl-alpha-(2-thienyl)benzeneethanamine dihydrochloride hemihydrate | 30.4 |
| 2-Amino-5-bromo-N-methyl-alpha-(3-methyl-2-thienyl)benzeneethanamine | 9.2 |
| Diphenylhydantoin (standard) | 3.9 |

Anticonvulsant activity is achieved when the compounds of this invention are administered to a subject requiring such treatment at an effective oral, parental or intravenous dose of from 1 to 50 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope of the practice of the invention.

In addition to elicting anticonvulsant responses, the 2-amino-α-arylphenethylamines of the present invention exhibit neuroprotective properties by virtue of their ability to antagonize N-methyl-D-aspartic acid (NMDA)-induced seizures (see D. M. Barnes in Science, 235, 632 (1987)) as demonstrated in the N-Methyl-D,L-Aspartic Acid Induced Seizure Assay. In this assay, male Swiss Webster mice (Charles River), 18–25 grams are used. Animals are ordered at 33 to 36 days of age and can be used for 8 days after arrival. They are housed for at least 24 hours in a climate controlled animal colony with food and water available ad libitum. On the day of testing, animals are brought to the laboratory and randomly assigned to groups. N-Methyl-D,L-aspartic acid (350 mg) is dissolved in 10 ml of saline and mixed thoroughly with a homogenizer for 1–2 minutes. Test compounds are prepared in distilled water and, if insoluable, a suitable surfactant is added. For a primary screen the test compound is administered at 60 mg/kg, ip (10 ml/kg), to groups of ten mice, 30 minutes prior to challenge with N-methyl-D,L-aspartic acid (350 mg/kg, sc). After N-Methyl-D,L-aspartic acid administration animals are placed individually in clear plastic cyclinders (12"×5.5"×¼") and then observed for clonic seizures. N-methyl-D,L-aspartic acid will produce clonic seizures, and sometimes tonic seizures and death, in vehicle control animals.

A clonic convulsion is defined as a single episode of clonic spasms of a least a 3 second duration. A tonic seizure is defined as a brief period of hindlimb flexion followed by a prolonged period of hindlimb extension. The mice treated with N-methyl-D,L-aspartic acid are considered "protected" when there is a total absence of clonic seizures during the 30 minute observation period.

A dose range determination is performed when 50% of the animals demonstrate protection in the primary screen. Test compounds are run at the time of peak effect. Three or more doses are used (10 animals per group).

Data is calculated by the method of J. T. Litchfield, Jr. and F. Wilcoxon. A test should be repeated if 40% of vehicle control animals are protected. The normalized percent formula is used when 10-30% of the vehicle control animals are protected.

The normalized percent protection is calculated using the following formula:

TABLE 3

$$\frac{\text{PERCENT PROTECTION OF DRUG GROUP} - \text{PERCENT PROTECTION OF VEHICLE CONTROL}}{100\% - \text{PERCENT PROTECTION OF VEHICLE CONTROL}} \times 100\%$$

| Compound | NMDA Protection ED$_{50}$ (mg/kg, ip) |
|---|---|
| 2-Amino-N-methyl-α-(3-methyl-2-thienyl)-benzeneethanamine | 26.7 |
| 2-Amino-N-methyl-α-(3-methyl-2-thienyl)-4-trifluoromethyl benzeneethanamine | 26.4 |
| 2-Amino-α-(3-methyl-3-thienyl)benzene-ethanamine | 19.0 |
| 2-Amino-5-phosphonovaleric acid | 48.5 |

Neuron protection activity is achieved when the compounds of this invention are administered to a subject requiring such treatment at an effective oral, parental or intravenous dose of from 1 to 50 mg/kg of body weight per day. It is to be understood, however, that for any particular subject specific dosage regimens should be adjusted according to the individual need and the professional judgement of the person administering or supervising the administration of the compounds of the invention. It is to be further understood that the dosages set forth herein are examples only and that they do not, to any extent, limit the scope of the practice of the invention.

The 2-amino-α-arylphenethylamines of the present invention are also useful as anxiolytics by virtue of their ability to reduce anxiety in mammals as demonstrated in the Geller Conflict Paradigm in Rats [Geller et al., Psychopharmacologia Berlin 1: 482-492, 1960], a standard assay for anxiolytic activity.

The intraperitoneal (i.p.) dosages at which the following compounds show anxiolytic activity are:

TABLE 4

| Compound | Dose (m.g./kg i.p.) | Anti-Conflict Response % Change Compared to Control |
|---|---|---|
| 2-amino-N-methyl-α-(3-methyl-2-thienyl)-benzeneethanamine | 20 | +807 |
|  | 40 | +547 |
|  | 60 | +242 |
| 2-amino-N-ethyl-α-(3-methyl-2-thienyl)-benzeneethanamine | 1 | +100 |
|  | 5 | +70 |
| Diazepam (standard) | 10 | +180 |
|  | 15 | +453 |
|  | 20 | +630 |

Antianxiety activity is achieved when the compounds of this invention are administered to a subject requiring such treatment at an effective oral, parenteral or intravenous dose of from 1 to 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

The compounds of this invention, while effective themselves, may be formulated and administered in the form of their pharmaceutically acceptable addition salts for the purposes of stability, convenience or crystallization, increased solubility and the like. Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Promogel ™, cornstarch and the like, a lubricant such as magnesium stearate or Sterotex; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the preceeding type, a liquid carrier such as a fatty oil. Other dosage unit forms may contain other various materials which modify the physical form of the dosage unit, for example, coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and nontoxic in the amounts used.

For the purposes of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzylalcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The parenteral preparation can be enclosed in ampules, disposable syringes or multiple dose vials made of glass or plastic.

Compounds of the invention include:
4,5-dihydro-4-(2-thienyl)-3H-1,3-benzodiazepine;
4,5-dihydro-2-methyl-4-(3-thienyl)-3H-1,3-benzodiazepine;
4,5-dihydro-2-cyclopropylmethyl-3-methyl-4-(3-thienyl)-3H-1,3-benzodiazepine;
4,5-dihydro-3-benzyl-2-methyl-4-(2-thienyl)-3H-1,3-benzodiazepine;
4,5-dihydro-2-(4-fluorophenyl)-3-methyl-4-(4-pyridinyl)-3H-1,3-benzodiazepine;
4,5-dihydro-2,3-dimethyl-4-(4-pyrazolyl)-3H-1,3-benzodiazepine;
4,5-dihydro-2-(1-propyl)-3-methyl-4-(4-pyrazolyl)-3H-1,3-benzodiazepine;
4,5-dihydro-2-ethyl-3-methyl-4-(2-pyrrolyl)-3H-1,3-benzodiazepine;
4,5-dihydro-2,3-dimethyl-8-hydroxy-4-(3-fluoro-2-thienyl)-3H-1,3-benzodiazepine;
2-amino-N-methyl-α-(4-methyl-2-thienyl)benzeneethanamine;
2-amino-N-methyl-α-(4-methyl-3-thienyl)benzeneethanamine;
2-amino-5-fluoro-N-methyl-α-(3-methyl-2-thienyl)benzeneethanamine;
2-amino-5-iodo-N-methyl-α-(3-methyl-2-thienyl)benzeneethanamine;
2-amino-N-methyl-5-trifluoromethyl-α-(3-methyl-2-thienyl)benzeneethanamine;
2-amino-5-methoxy-N-methyl-α-(3-methyl-2-thienyl)benzeneethanamine;
2-amino-5-methyl-N-methyl-α-(3-methyl-2-thienyl)benzeneethanamine;
2-amino-4-fluoro-N-methyl-α-(3-methyl-2-thienyl)benzeneethanamine;
2-amino-4-chloro-N-methyl-α-(3-methyl-2-thienyl)benzeneethanamine;
2-amino-4-bromo-N-methyl-α-(3-methyl-2-thienyl)benzeneethanamine;
2-amino-4-iodo-N-methyl-α-(3-methyl-2-thienyl)benzeneethanamine;
2-amino-N-methyl-α-(3-methyl-2-thienyl)-4-trifluoromethylbenzeneethanamine;
2-amino-4-methoxy-N-methyl-α-(3-methyl-2-thienyl)benzeneethanamine;
2-amino-4-methyl-N-methyl-α-(3-methyl-2-thienyl)benzeneethanamine;
2-amino-N-methyl-α-(1-methyl-2-pyrrolyl)benzeneethanamine;
2-amino-N-methyl-α-(1-methyl-3-pyrrolyl)benzeneethanamine;
2-amino-α-(4-pyrazolyl)-N-methylbenzeneethanamine;
2-amino-N-methyl-α-(2-thiazolyl)benzeneethanamine;
2-amino-N-methyl-α-(4-thiazolyl)benzeneethanamine;
2-amino-N-methyl-α-(5-thiazolyl)benzeneethanamine;
2-amino-N-methyl-α-(2-methyl-4-thiazolyl)benzeneethanamine;
2-amino-N-methyl-α-(5-methyl-2-thiazolyl)benzeneethanamine;
2-amino-N-methyl-α-(2-methyl-5-thiazolyl)benzeneethanamine;
2-amino-α-(3-pyrazolyl)-N-methylbenzeneethanamine;
2-amino-α-(2-chloro-4-thiazolyl)-N-methylbenzeneethanamine;
2-amino-α-(5-chloro-2-thiazolyl)-N-methylbenzeneethanamine;
4-amino-α-(2-chloro-4-thiazolyl)-N-methylbenzeneethanamine;
2-amino-N-methyl-α-(4-pyrazolyl)benzeneethanamine;
2-amino-N-methyl-α-(3-pyrazolyl)benzeneethanamine;
2-amino-α-(2-imidazolyl)-N-methylbenzeneethanamine;
N-formyl-2-hydroxy-N-methyl-α-(3-methyl-2-thienyl)benzeneethanamine;
2-hydroxy-N-methyl-α-(3-methyl-2-thienyl)benzeneethanamine;
2-methoxy-N-methyl-α-(3-methyl-2-thienyl)benzeneethanamine;
N,N-dimethyl-2-methylamino-α-(3-methyl-2-thienyl)benzeneethanamine;
4,5-dihydro-4-(2-thienyl)-3H-1,3-benzodiazepine;
4,5-dihydro-3-methyl-4-(2-thienyl)-3H-1,3-benzodiazepine;
4,5-dihydro-2-methyl-4-(2-thienyl)-3H-1,3-benzodiazepine;
4,5-dihydro-2-ethyl-7-fluoro-3-methyl-4-(3-methyl-2-thienyl)-3H-1,3-benzodiazepine;
7-chloro-4,5-dihydro-2-ethyl-3-methyl-4-(3-methyl-2-thienyl)-3H-1,3-benzodiazepine;
7-bromo-4,5-dihydro-2-ethyl-3-methyl-4-(3-methyl-2-thienyl)-3H-1,3-benzodiazepine;
4,5-dihydro-2-ethyl-3-methyl-4-(3-methyl-2-thienyl)-7-trifluoromethyl-3H-1,3-benzodiazepine;
4,5-dihydro-3,7-dimethyl-2-ethyl-4-(3-methyl-2-thienyl)-3H-1,3-benzodiazepine;
4,5-dihydro-2-ethyl-7-methoxy-4-(3-methyl-2-thienyl)-3H-1,3-benzodiazepine;
4,5-dihydro-2-ethyl-8-methoxy-4-(3-methyl-2-thienyl)-3H-1,3-benzodiazepine;
8-chloro-4,5-dihydro-2-ethyl-3-methyl-4-(3-methyl-2-thienyl)-3H-1,3-benzodiazepine;
4,5-dihydro-2-ethyl-3-methyl-4-(1-methyl-2-pyrrolyl)-3H-1,3-benzodiazepine;
4,5-dihydro-2-ethyl-3-methyl-4-(1-methyl-3-pyrrolyl)-3H-1,3-benzodiazepine;

4,5-dihydro-2-ethyl-3-methyl-4-(2-thiazolyl)-3H-1,3-benzodiazepine;

4,5-dihydro-2-ethyl-3-methyl-4-(4-thiazolyl)-3H-1,3-benzodiazepine;

4,5-dihydro-2-ethyl-3-methyl-4-(5-thiazolyl)-3H-1,3-benzodiazepine;

2-cyclopropyl-4,5-dihydro-3-methyl-4-(3-methyl-2-thienyl)-3H-1,3-benzodiazepine;

3-benzyl-4,5-dihydro-2-ethyl-4-(2-thienyl)-3H-1,3-benzodiazepine;

4,5-dihydro-2-(4-fluorophenyl)-3-methyl-4-(4-pyridinyl)-3H-1,3-benzodiazepine;

4,5-dihydro-2-ethyl-3-methyl-4-(4-pyrazolyl)-3H-1,3-benzodiazepine;

4,5-dihydro-2-ethyl-3-methyl-4-(3-pyrazolyl)-3H-1,3-benzodiazepine;

4,5-dihydro-2-ethyl-4-(2-imidazolyl)-3-methyl-3H-1,3-benzodiazepine; and 2-amino-α-(4-chloro-2-thiazolyl)-N-methylbenzeneethanamine.

EXAMPLES

The following examples are for illustrative purposes only and are not to be construed as limiting the invention. All percentages are by volume, unless otherwise noted.

EXAMPLE 1

N-[2-[2-Methylamino-2-(2-thienyl)ethyl]phenyl]-2,2-dimethylpropanamide

A stirred, chilled (−10° C.) solution of 19.3 g of N-[(2-methyl)phenyl]-2,2-dimethylpropanamide in 150 ml of tetrahydrofuran was treated over 43 min with 140 ml of a 1.6M solution of n-butyllithium in hexane, while maintaining the temperature at or below 0° C. Stirring for 2.3 hours with cooling afforded a suspension. The stirred, cooled (−6° C.) suspension was treated over 13 min with a solution of 15.02 g of N-(2-thienylmethylene)methanamine in 30 ml of toluene. The reaction mixture was stirred with cooling (1° C.) for 1.5 hours, quenched by the addition of 120 ml of water and concentrated. The concentrate was extracted with dichloromethane (2×200 ml), and the combined extract was dried over anhydrous sodium sulfate, filtered, and evaporated to an oil. Preliminary purification of the oil was achieved by preparative high pressure liquid chromatography (hereinafter "HPLC") separations utilizing a Water's Model 500A High Pressure Liquid Chromatograph (silica gel; eluting with 10% methanol in ethyl acetate). The appropriate fractions from each separation were combined and concentrated to an oil. The purification procedure was repeated utilizing 5% methanol in ethyl acetate as the eluent to yield 11.71 g of N-[2-[2-methylamino-2-(2-thienyl)ethyl]phenyl]-2,2-dimethylpropanamide as a solid, mp 78.5°–82° C.

ANALYSIS: Calculated for $C_{18}H_{24}N_2OS$: 68.32%C; 7.64%H; 8.85%N; Found: 67.96%C; 7.69%H; 8.74%N.

EXAMPLE 2

2-Amino-N-methyl-α-(2-thienyl)benzeneethanamine dihydrochloride hemihydrate

A stirred suspension of 11.28 g of N-[2-[2-methylamino-2-(2-thienyl)ethyl]phenyl]-2,2-dimethylpropanamide in 100 ml of 6N hydrochloric acid was refluxed under nitrogen for 8 hours. The mixture was cooled, decanted over crushed ice and water (200 ml), basified by the addition of 50% sodium hydroxide solution, and extracted with dichloromethane (3×150 ml). The combined extract was dried over anhydrous sodium sulfate, filtered, and concentrated to an oil. The oil was purified by means of HPLC on a Water's Model 500A High Pressure Liquid Chromatograph (silica gel) utilizing methanol as the eluent. Concentration of the appropriate fractions yielded 5.96 g of 2-amino-N-methyl-α-(2-thienyl)benzeneethanamine. A sample of the product (2 g) in methanol (5 ml) was treated with ethereal hydrogen chloride and a solid was precipitated by further dilution with anhydrous ether. Recrystallization from absolute ethanol gave 2.12 g of 2-amino-N-methyl-α-(2-thienyl)benzeneethanamine dihydrochloride hemihydrate, mp 210°–215° C. (dec.).

ANALYSIS: Calculated for $C_{13}H_{16}N_2S \cdot 2HCl \cdot 0.5H_2O$: 49.68%C; 6.09%H; 8.91%N; Found: 49.32%C; 5.94%H; 8.87%N.

EXAMPLE 3

4,5-Dihydro-2,3-dimethyl-4-(2-thienyl)-3H-1,3-benzodiazepine

A stirred solution of 3.06 g of 2-amino-N-methyl-α-(2-thienyl)benzeneethanamine (prepared as described in Example 2) and 12.72 g of triethyl orthoacetate was treated rapidly with 5 ml of glacial acetic acid. The resulting solution was refluxed for 8 hours and allowed to stand at room temperature overnight. The solution was concentrated on a rotary evaporator and the residual syrup was dissolved in 50 ml of 10% hydrochloric acid. The solution was washed with diethyl ether (2×30 ml), basified with 10% sodium hydroxide solution, and extracted with dichloromethane (2×50 ml). The combined organic phase was dried over anhydrous sodium sulfate, filtered, and concentrated to an oil which crystallized under refrigeration. The crystalline product was purified by HPLC (Water's Associates Prep LC/System 500A; silica gel; sample applied in dichloromethane; 2% triethylamine in methanol as the eluent). Concentration of the appropriate fractions yielded an oil which crystallized on trituration with hexane. The compound was isolated, washed with hexane, and dried in vacuo at room temperature to afford 2.05 g of 4,5-dihydro-2,3-dimethyl-4-(2-thienyl)-3H-1,3-benzodiazepine, mp 106.5°–108.5° C.

ANALYSIS: Calculated for $C_{15}H_{16}N_2S$: 70.28%C; 6.29%H; 10.93%N; Found: 70.61%C; 6.30%H; 10.91%N.

EXAMPLE 4

4,5-Dihydro-3-methyl-2-(1-methylethyl)-4-(2-thienyl)-3H-1,3-benzodiazepine hydrochloride A stirred solution of 3.45 g of 2-amino-N-methyl-α-(2-thienyl)benzeneethaneamine and 13.34 g of trimethyl orthoisobutyrate was treated rapidly with 3.8 ml of glacial acetic acid. The reaction mixture was refluxed for 8 hours and cooled to room temperature overnight. The mixture was concentrated on a rotary evaporator at 70° C. After standing overnight under refrigeration, the residue was dissolved in 60 ml of 10% hydrochloric acid solution and extracted with diethyl ether (2×50 ml). The aqueous phase was basified with 10% sodium hydroxide solution and extracted with dichloromethane (2×75 ml). The combined organic phase was dried over anhydrous sodium sulfate, filtered, and concentrated to an oil. The oil was purified by HPLC (Water's Associates Prep LC/System 500; silica gel; sample applied in dichloromethane; methanol as eluent). Concentration of the appropriate fractions yielded 1.08 g of 4,5-dihydro-3-methyl-2-(1-methylethyl)-4-(2-thienyl)-3H-1,3-benzodiazepine as an oil.

The oil was dissolved in methanol (2 ml) and the solution was treated with a slight excess of ethereal hydrogen chloride, followed by dilution with 40 ml of anhydrous diethyl ether. Upon dilution, separate oil and ether phases formed. The oil phase was separated and triturated with three successive portions of diethyl ether to afford a semisolid which was recrystallized from propionitrile to yield 0.54 g of crystalline solid. Work-up of propionitrile mother liquor afforded an additional 0.24 g of crystals. The final propionitrile mother liquor and combined ethereal phases were concentrated to an oil which was recrystallized from propionitrile to yield an additional 0.11 g of crystals. The three crops of crystals were mixed together to yield 0.89 of 4,5-dihydro-3-methyl-2-(1-methylethyl)-4-(2-thienyl)-3H-1,3-benzodiazepine hydrochloride, mp 202°–205.5° C.

ANALYSIS: Calculated for $C_{17}H_{20}N_2S \cdot HCl$: 63.63%C; 6.60%H; 8.73%N; Found: 63.43%C; 6.62%H; 8.72%N.

EXAMPLE 5

4,5-Dihydro-3-methyl-2-(1-propyl)-4-(2-thienyl)-3H-1,3-benzodiazepine hydrochloride A stirred solution of 3.36 g of 2-amino-N-methyl-α-(2-thienyl)benzeneethanamine (prepared as described in Example 2) and 12.89 g of trimethyl orthobutyrate was treated rapidly with 3.5 ml of glacial acetic acid. The resulting solution was refluxed for 8 hours, cooled, and concentrated on a rotary evaporator at 70° C. The residue was partitioned between 10% hydrochloric acid solution and diethyl ether. After extraction of the aqueous phase with a second portion of diethyl ether, the solution was basified with 10% sodium hydroxide solution and extracted with dichloromethane (2×100 ml).

The combined organic phase was dried over anhydrous sodium sulfate, filtered, and concentrated to an oil. The oil was purified by HPLC (Water's Associates Prep LC/System 500; silica gel; and eluted with methanol followed by 2% triethylamine in methanol). Concentration of the appropriate fractions yielded 2.85 g of 4,5-dihydro-3-methyl-2-(1-propyl)-4-(2-thienyl)-3H-1,3-benzodiazepine as an oil.

The oil was dissolved in diethyl ether and treated with ethereal hydrogen chloride. The resulting precipitate was triturated with diethyl ether until solidification was complete, isolated by vacuum filtration, and dried in vacuo at 40° C. Recrystallization from acetonitrile yielded 2.21 g of 4,5-dihydro-3-methyl-2-(1-propyl)-4-(2-thienyl)-3H-1,3-benzodiazepine hydrochloride, mp 222°–223.5° C.

ANALYSIS: Calculated for $C_{17}H_{20}N_2S \cdot HCl$: 63.63%C; 6.60%H; 8.73%N; Found: 63.49%C; 6.60%H; 8.75%N.

EXAMPLE 6

N-[2-[2-(Methylamino)-2-(3-thienyl)ethyl]phenyl]-2,2-dimethylpropanamide

To a chilled, solution (−50° C.) of 19.13 g of 2,2-dimethyl-N-[(2-methyl)phenyl]propanamide in 200 ml of tetrahydrofuran was added, dropwise over 1.5 hours, 88 ml of a 2.5M solution of n-butyllithium in hexane. Upon completion of the addition, the resultant solution was stirred for 2 hours with cooling. A solution of 15.0 g of 3-thiophene-carboxaldehyde methylimine in 30 ml of toluene, was then added, dropwise over 15 minutes, to the cooled solution. Upon completion of the 3-thiophenecarboxaldehyde methylimine addition, the reaction mixture was stirred for 20 minutes at 0° C., quenched by the addition of 300 ml of water, concentrated, and extracted with dichloromethane. The combined extract was dried over anhydrous magnesium sulfate, filtered, and concentrated to an oil. HPLC of the oil (Water's Associates Prep LC/System 500; silica gel; methanol as the eluent) afforded a semipurified product which was subsequently chromatographed under otherwise identical conditions utilizing ethyl acetate, followed by methanol as eluents. Concentration of the appropriate fractions and trituration with hexane yielded 18.0 g of N-[2-[2-(methylamino)-2-(3-thienyl)ethyl]phenyl]-2,2-dimethylpropanamide. mp 81°–84° C.

ANALYSIS: Calculated for $C_{18}H_{24}N_2OS$: 68.32%C; 7.64%H; 8.85%N; Found: 68.25%C; 7.75%H; 8.71%N.

EXAMPLE 7

2-Amino-N-methyl-α-(3-thienyl)benzeneethanamine

A solution of 11.0 g of N-[2-[2-(methylamino)-2-(3-thienyl)ethyl]phenyl-2,2-dimethylpropanamide in 150 ml of 6N hydrochloric acid was refluxed for 8 hours. The solution was then decanted into an ice-water mixture (500 ml) and basified with 50% sodium hydroxide solution. The aqueous mixture was extracted with dichloromethane, dried over anhydrous magnesium sulfate and concentrated to an oil.

Purification was accomplished by preparative HPLC (Water's Associates Prep LC/System 500, silica gel, methanol eluent). Concentration of the appropriate fractions yielded 3.21 g of 2-amino-N-methyl-α-(3-thienyl)benzeneethanamine as an oil.

ANALYSIS: Calculated for $C_{13}H_{16}N_2S$: 67.20%C; 6.94%H; 12.06%N; Found: 67.17%C; 6.93%H; 11.84%N.

EXAMPLE 8

4,5-Dihydro-2,3-dimethyl-4-(3-thienyl)-3H-1,3-benzodiazepine

A solution of 6.50 g of 2-amino-N-methyl-α-(3-thienyl)benzeethanamine and 15.5 ml of triethyl orthoacetate was treated with glacial acetic acid (9 ml). After refluxing for eight hours, the volatile components were removed at 70° C. on a rotary evaporator. The residual oil was decanted into an ice-water mixture and basified with 10% sodium hydroxide solution. The aqueous mixture was extracted with dichloromethane and the organic phase was dried over anhydrous magnesium sulfate and concentrated to an oil.

Purification was accomplished by preparative HPLC (Water's Associates Prep LC/System 500, silica gel, elution with 2% triethylamine in methanol). Concentration of the appropriate fractions afforded a solid which was triturated with hexane and dried in vacuo at 50° C. to yield 3.79 g of 4,5-dihydro-2,3-dimethyl-4-(3-thienyl)-3H-1,3-benzodiazepine, mp 113°–117° C.

ANALYSIS: Calculated for $C_{15}H_{16}N_2S$: 70.27%C; 6.29%H; 10.93%N; Found: 69.88%C; 6.30%H; 10.82%N.

EXAMPLE 9

4,5-Dihydro-2-ethyl-3-methyl-4-(2-thienyl)-3H-1,3-benzodiazepine hydrochloride A stirred solution of 2.47 g of 2-amino-N-methyl-α-(2-thienyl)benzeneethanamine and 11.21 g of triethyl orthopropionate was treated rapidly with glacial acetic acid (4 ml). The solution was refluxed for 5 hours, allowed to stand overnight at room temperature, and concentrated on a rotary evaporator. A solution of the residual oil and 10% hydrochloric acid (50 ml) was extracted with ether (2×50 ml), basified with 10% sodium hydroxide solution and extracted with dichloromethane (2×50 ml). The combined organic phase was dried over anhydrous sodium sulfate, filtered, and concentrated to an oil.

Purification was accomplished by preparative HPLC (Water's Associates Prep LC/System 500, silica gel, sample applied in dichloromethane, and eluted with 2% triethylamine in methanol). Concentration of the appropriate fractions yielded 4,5-dihydro-2-ethyl-3-methyl-4-(2-thienyl)-3H-1,3-benzodiazepine as an oil. The oil was solubilized in 30 ml of anhydrous diethyl ether and treated with excess ethereal hydrogen chloride to precipitate the corresponding hydrochloride salt. The precipitate was washed with ether, isolated by vacuum filtration, washed again with ether and dried in vacuo at 40° C. over sodium hydroxide pellets to give 1.86 g of 4,5-dihydro-2-ethyl-3-methyl-4-(2-thienyl)-3H-1,3-benzodiazepine hydrochloride, mp 216°-219° C.

ANALYSIS: Calculated for $C_{16}H_{18}N_2S \cdot HCl$: 62.63%C; 6.24%H; 9.13%N; Found: 62.24%C; 6.24%H; 9.02%N.

EXAMPLE 10

4,5-Dihydro-3-methyl-2-(1-propyl)-4-(3-thienyl)-3H-1,3-benzodiazepine

A solution of 4.80 g of 2-amino-N-methyl-α-(3-thienyl)benzeneethanamine and 18.35 ml of trimethyl orthobutyrate was treated with 6.90 ml of glacial acetic acid. After refluxing for 8 hours, the volatile components were removed on a rotary evaporator. The residual oil was acidified with 10% hydrochloric acid solution, and extracted with diethyl ether (2×100 ml). The aqueous layer was basified with 10% sodium hydroxide solution, and extracted with dichloromethane (3×100 ml). The organic phase was dried over anhydrous sodium sulfate, filtered, and evaporated to an oil.

Purification was accomplished by preparative HPLC (Water's Associates Prep LC/System 500A, silica gel, elution with 2% triethylamine in methanol). Concentration of the appropriate fractions yielded an oil which solidified under refrigeration. Trituration of the solid with hexane afforded granular crystals which were collected, washed with hexanes, and dried in vacuo to yield 4.08 g of 4,5-dihydro-3-methyl-2-(1-propyl)-4-(3-thienyl)-3H-1,3-benzodiazepine, mp 44.5°-46.5° C.

ANALYSIS: Calculated for $C_{17}H_{20}N_2S$: 71.78%C; 7.09%H; 9.85%N; Found: 71.65%C; 6.94%H; 9.92%N.

EXAMPLE 11

4,5-Dihydro-3-methyl-2-(1-methylethyl)-4-(3-thienyl)-3H-1,3-benzodiazepine hydrochloride monohydrate A solution of 4.78 g of 2-amino-N-methyl-α-(3-thienyl)benzeneethanamine and 16.77 g of trimethyl orthoisobutyrate was treated with glacial acetic acid (6.87 ml). After refluxing for 8 hours, the volatile components were removed on a rotary evaporator. The residual oil was acidified with 10% hydrochloric acid aqueous solution and extracted with diethyl ether (2×100 ml). The aqueous solution was basified with 10% sodium hydroxide aqueous solution to a pH of 12, and extracted with dichloromethane (3×100 ml). The combined dichloromethane layers were washed with 100 ml of water, dried over anhydrous sodium sulfate, and concentrated to an oil.

Purification was accomplished by preparative HPLC (Water's Associates Prep LC/System 500A; silica gel; elution with 2% triethylamine/methanol). Concentration of the appropriate fractions yielded 4,5-dihydro-3-methyl-2-(1-methylethyl)-4-(3-thienyl)-3H-1,3-benzodiazepine. The oil was converted to the corresponding hydrochloride salt which was triturated with ether to yield 2.90 g of 4,5-dihydro-3-methyl-2-(1-methylethyl)-4-(3-thienyl)-3H-1,3-benzodiazepine hydrochloride monohydrate, mp 119°-122° C.

ANALYSIS: Calculated for $C_{17}H_{20}N_2S \cdot HCl \cdot H_2O$: 60.24%C; 6.84%H; 8.27%N; Found: 60.20%C; 6.59%H; 8.31%N;

EXAMPLE 12

4,5-Dihydro-3-methyl-2-phenyl-4-(3-thienyl)-3H-1,3-benzodiazepine hydrochloride A solution of 6.50 g of 2-amino-N-methyl-α-(3-thienyl)benzeethanamine and 14.5 ml of trimethyl orthobenzoate was treated with glacial acetic acid (9 ml). After refluxing for eight hours, the volatile components were removed at 70° C. on a rotary evaporator. The residual oil was decanted into an ice-water mixture and basified with 10% sodium hydroxide solution. The aqueous mixture was extracted with dichloromethane and the organic phase was dried over anhydrous magnesium sulfate, filtered, and concentrated to an oil.

Purification was accomplished by preparative HPLC (Water's Associates Prep LC/System 500A, silica gel, eluted with methanol). Concentration of the appropriate fractions yielded 4,5-dihydro-3-methyl-2-phenyl-4-(3-thienyl)-3H-1,3-benzodiazepine as an oil. The oil was dissolved in methanol and treated dropwise with ethereal hydrogen chloride to precipitate the corresponding hydrochloride salt. The salt was collected by vacuum filtration, washed with ether, and dried overnight under vacuum to yield 4.49 g of 4,5-dihydro-3-methyl-2-phenyl-4-(3-thienyl)-3H-1,3-benzodiazepine hydrochloride, mp 266°-269° C.

ANALYSIS: Calculated for $C_{20}H_{18}N_2S \cdot HCl$: 67.68%C; 5.40%H; 7.90%N; Found: 67.26%C; 5.46%H; 7.78%N;

EXAMPLE 13

4,5-Dihydro-2-ethyl-3-methyl-4-(3-thienyl)-3H-1,3-benzodiazepine hydrochloride A solution of 6.00 g of 2-amino-N-methyl-α-(3-thienyl)benzeneethanamine and 10 ml of triethyl orthopropionate, was treated with 8 ml of glacial acetic acid. After refluxing for eight hours, the volatile components were removed at 70° C. on a rotary evaporator. The residual oil was decanted into an ice-water mixture and basified with 10% sodium hydroxide solution. The aqueous mixture was extracted with dichloromethane and the organic phase was dried over anhydrous magnesium sulfate, filtered, and concentrated to provide 4,5-dihydro-2-ethyl-3-methyl-4-(3-thienyl)-3H-1,3-benzodiazepine as an oil.

Purification was accomplished by preparative HPLC (Water's Associates Prep LC/System 500A, silica gel, utilizing with 2% triethylamine in methanol as the eluent). Concentration of the appropriate fractions yielded an oil which was dissolved in methanol and treated dropwise with ethereal hydrogen chloride. The resultant precipitate was washed with ether and dried in vacuo to yield 3.89 g of 4,5-dihydro-2-ethyl-3-methyl-4-(3-thienyl)-3H-1,3-benzodiazepine hydrochloride, mp 242°-244° C.

ANALYSIS: Calculated for $C_{16}H_{18}N_2S \cdot HCl$: 62.63%C; 6.24%H; 9.13%N; Found: 62.71%C; 6.26%H; 9.06%N.

EXAMPLE 14

N-[2-[2-(Methylamino)-2-(3-methyl-2-thienyl)ethyl]phenyl]-2,2-dimethylpropanamide A chilled solution (−6° C.) of 76.0 g of 2,2-dimethyl-N-[(2-methyl)phenyl]propanamide in 600 ml of tetrahydrofuran was treated dropwise over 1.25 hours with 344 ml of a 2.5M solution of n-butyllithium in hexanes. After the addition was complete, the resultant solution was stirred for 2 hours with cooling and then was treated dropwise over 20 minutes, with a solution of 6.0 g of 3-methyl-2-thiophenecarboxaldehyde methylimine in 30 ml of toluene. After the addition was complete, the mixture was stirred for an additional 20 minutes. The reaction was quenched by the rapid addition of water. After concentration to remove the organic solvents, the residual oil-water mixture was extracted with dichloromethane. The combined organic phase was dried over anhydrous magnesium sulfate, filtered, and concentrated to an oil.

Purification was accomplished by preparative HPLC (Water's Associates Prep LC/System 500, silica gel, eluted with ethyl acetate). Concentration of the appropriate fractions afforded an oil which was further purified by preparative HPLC to yield 70 g of N-[2-[2-(methylamino)-2-(3-methyl-2-thienyl)ethyl]phenyl]-2,2-dimethylpropanamide as an oil.

ANALYSIS: Calculated for $C_{19}H_{26}N_2OS$: 69.05%C; 7.93%H; 8.48%N; Found: 68.80%C; 7.80%H; 8.13%N.

EXAMPLE 15

2-Amino-N-methyl-α-(3-methyl-2-thienyl)benzeneethanamine

A solution of 35.0 g of N-[2-[2-(methylamino)-2-(3-methyl-2-thienyl)ethyl]phenyl]-2,2-dimethylpropanamide in 600 ml of 6N hydrochloric acid was refluxed for 8 hours. The solution was then decanted into an ice-water mixture and basified with 50% sodium hydroxide solution. The aqueous mixture was extracted with dichloromethane (2 L), dried over anhydrous magnesium sulfate and concentrated to an oil.

Purification was accomplished by preparative HPLC (Water's Associates Prep LC/System 500A, silica gel, eluted with methanol). Concentration of the appropriate fractions yielded 6.42 g of 2-amino-N-methyl-α-(3-methyl-2-thienyl)benzeneethanamine as an oil.

ANALYSIS: Calculated for $C_{14}H_{18}N_2S$: 68.25%C; 7.36%H; 11.37%N; Found: 68.35%C; 7.26%H; 11.35%N.

EXAMPLE 16

4,5-Dihydro-2,3-dimethyl-4-(3-methyl-2-thienyl)-3H-1,3-benzodiazepine hydrochloride monohydrate A solution of 4.42 g of 2-amino-N-methyl-α-(3-methyl-2-thienyl)benzeneethanamine and 10 ml of triethyl orthoacetate was treated with glacial acetic acid (8 ml). After refluxing for eight hours, the volatile components were removed at 70° C. on a rotary evaporator. The residual oil was decanted into an ice-water mixture and basified with 10% sodium hydroxide solution. The aqueous mixture was extracted with dichloromethane, dried over anhydrous magnesium sulfate and concentrated to an oil.

Purification was accomplished by preparative HPLC (Water's Associates Prep LC/System 500, silica gel, eluted with 2% triethylamine in methanol). Concentration of the appropriate fractions yielded 4,5-dihydro-2,3-dimethyl-4-(3-methyl-2-thienyl)-3H-1,3-benzodiazepine as an oil. The corresponding hydrochloride salt was made by dissolving the oil in methanol and treating with ethereal hydrogen chloride. After diluting with anhydrous ether, a precipitate separated. The solid was collected and dried overnight at 40° C. under vacuum to yield 2.52 g of 4,5-dihydro-2,3-dimethyl-4-(3-methyl-2-thienyl)-3H-1,3-benzodiazepine hydrochloride monohydrate, mp 140°-142° C.

ANALYSIS: Calculated for $C_{16}H_{18}N_2S \cdot HCl \cdot H_2O$: 59.14%C; 6.51%H; 8.62%N; Found: 59.36%C; 6.25%H; 8.56%N.

EXAMPLE 17

4,5-Dihydro-2-ethyl-3-methyl-4-(3-methyl-2-thienyl)-3H-1,3-benzodiazepine hydrochloride monohydrate A stirred solution of 2.94 g of 2-amino-N-methyl-α-(3-methyl-2-thienyl)benzeneethanamine and 12.58 g of triethyl orthopropionate was treated rapidly with glacial acetic acid (4.0 ml). The solution was refluxed for 8 hours, cooled to room temperature and concentrated on a rotary evaporator at 80° C. The residue was slurried with ether and treated with 50 ml of 10% hyrochloric acid solution. The aqueous phase was washed with ether, basified with 10% sodium hydroxide solution (60 ml), and extracted with dichloromethane (2×50 ml). The combined organic phase was dried over anhydrous sodium sulfate, filtered and concentrated to an oil.

Purification was accomplished by preparative HPLC (Water's Associates Prep LC/System 500A; silica gel; sample applied in dichloromethane (20 ml); elution with 2% triethylamine in methanol. Concentration of the appropriate fractions yielded 4,5-dihydro-2-ethyl-3-methyl-4-(3-methyl-2-thienyl)-3H-1,3-benzodiazepine as an oil. The oil was dissolved in methanol (5 ml) and ether (2 ml), and the resulting solution treated with a slight excess of ethereal hydrogen chloride. Further dilution with ether precipitated the corresponding hydrochloride salt. The precipitate was isolated by vacuum filtration, washed twice with ether, and dried in vacuo at 40° C. to yield 1.9 g of 4,5-dihydro-2-ethyl-3-methyl-4-(3-methyl-2-thienyl)-3H-1,3-benzodiazepine hydrochloride monohydrate, mp 185°-206° C.

ANALYSIS: Calculated for $C_{17}H_{20}N_2S \cdot HCl \cdot H_2O$: 60.25%C; 6.84%H; 8.27%N; Found: 60.15%C; 6.88%H; 8.46%N.

EXAMPLE 18

4,5-Dihydro-3-methyl-2-(1-methylethyl)-4-(3-methyl-2-thienyl)-3H-1,3-benzodiazepine hydrochloride A solution of 5.86 g of 2-amino-N-methyl-α-(3-methyl-2-thienyl)benzeneethanamine and 19.56 g of trimethyl orthoisobutyrate was treated rapidly with 7.94 ml of glacial acetic acid. The solution was refluxed for 8 hours under nitrogen and concentrated on a rotary evaporator at 40° C. The residual oil was acidified with 10% hydrochloric acid solution and extracted with ether (3×100 ml). The aqueous phase was basified with 10% sodium hydroxide solution and extracted with dichloromethane (3×100 ml). The organic phases was dried over anhydrous sodium sulfate, filtered and concentrated to an oil. Purification was accomplished by HPLC (Water's Associates Prep LC/System 500A, silica gel, utilizing methanol followed by 2% triethylamine in methanol as successive eluents). Concentration of the appropriate fractions yielded 1.88 g of 4,5-dihydro-3-methyl-2-(1-methylethyl)-4-(3-methyl-2-thienyl)-3H-1,3-benzodiaze pine as an oil. The oil was treated with ethereal hydrogen chloride and the resulting precipitate was triturated with ether to yield 1.80 g of 4,5-dihydro-3-methyl-2-(1-methylethyl)-4-(3-methyl-2-thienyl)-3H-1,3-benzodiazepine hydrochloride, mp 240.5°-241.0° C.

ANALYSIS: Calculated for $C_{18}H_{22}N_2S \cdot HCl$: 64.55%C; 6.92%H; 8.37%N; Found: 64.28%C; 6.96%H; 8.27%N.

EXAMPLE 19

4,5-Dihydro-3-methyl-4-(3-methyl-2-thienyl)-2-phenyl-3H-1,3-benzodiazepine hydrochloride A stirred solution of 2.19 g of 2-amino-N-methyl-α-(3-methyl-2-thienyl)benzeneethanamine and 9.88 g of trimethyl orthobenzoate was treated rapidly with 2.4 ml of glacial acetic acid, and heated under reflux for 8 hours. The solution was concentrated at 75° C. on a rotary evaporator (vacuum pump) to a syrup. The syrup was then partioned between 10% hydrochloric acid solution (50 ml) and ether. The aqueous phase was extracted again with ether, basified with 10% sodium hydroxide solution (60 ml) and extracted with dichloromethane (2×100 ml). The combined organic phase was dried over anhydrous sodium sulfate, filtered, and concentrated to an oil. The oil was purified by preparative HPLC (Water's Associates Prep LC/System 500A, silica gel, sample applied in dichloromethane, 2% triethylamine in methanol as the eluent). Concentration of the appropriate fractions yielded 2.70 g of 4,5-dihydro-3-methyl-4-(3-methyl-2-thienyl)-2-phenyl-3H-1,3-benzodiazepine as an oil.

A solution of the oil and methanol (5 ml) was treated with a slight excess of ethereal hydrogen chloride. Further dilution with ether precipitated the corresponding hydrochloride salt. The precipitate was isolated and dried in vacuo at 40° C. to yield 2.13 g of 4,5-dihydro-3-methyl-4-(3-methyl-2-thienyl)-2-phenyl-3H-1,3-benzodiazepine hydrochloride, mp 221°-224° C.

ANALYSIS: Calculated for: $C_{21}H_{20}N_2S \cdot HCl$: 68.37%C; 5.74%H; 7.59%N; Found: 67.95%C; 6.01%H; 7.57%N.

EXAMPLE 20

N-[2-[2-(Methylamino)-2-(2-pyridinyl)ethyl]phenyl]-2,2-dimethylpropanamide

A chilled solution (−5° C.) of 38.26 g of 2,2-dimethyl-N-[(2-methyl)phenyl]propanamide in 300 ml of tetrahydrofuran was treated dropwise over 1.25 hour with 176 ml of a 2.5M solution of n-butyllithium in hexanes. After the addition was complete, the resultant solution was stirred for 2.5 hours with cooling and then was treated dropwise over 15 minutes with a solution of 28.84 g of 2-pyridinecarboxaldehyde methylimine in 60 ml of toluene. The solution was stirred for an additional 15 minutes, quenched by the rapid addition of water (250 ml), and concentrated. The residue was extracted with dichloromethane (750 ml). The organic phase was dried over anhydrous magnesium sulfate, and concentrated to an oil.

Purification was accomplished by preparative HPLC (Water's Associates Prep LC/System 500, silica gel, elution with methanol). Concentration of the appropriate fractions yielded an oil which was further purified by preparative HPLC until free of impurities to yield 10 g of N-[2-[2-(methylamino)-2-(2-pyridinyl)ethyl]phenyl]-2,2-dimethylpropanamide as an oil.

ANALYSIS: Calculated for $C_{19}H_{25}N_3O$: 73.28%C; 8.09%H; Found: 72.84%C; 7.89%H.

EXAMPLE 21

2-Amino-N-methyl-α-(2-pyridinyl)benzeneethanamine

A solution of 8.0 g of N-[2-[2-(methylamino)-2-(2-pyridinyl)ethyl]phenyl]-2,2-dimethylpropanamide in 100 ml of 6N hydrochloric acid was refluxed for 8 hours. The solution was then decanted into ice-water (250 ml) and basified with 50% sodium hydroxide solution. The aqueous mixture was extracted with dichloromethane (500 ml), dried over anhydrous magnesium sulfate and concentrated to an oil.

Purification was accomplished by preparative HPLC (Water's Associates Prep LC/System 500, silica gel, elution with methanol). Concentration of the appropriate fractions yielded 2.5 g of 2-amino-N-methyl-α-(2-pyridinyl)benzeneethanamine as an oil.

ANALYSIS: Calculated for $C_{14}H_{17}N_3$: 73.98%C; 7.54%H; Found: 73.74%C; 7.54%H.

EXAMPLE 22

4,5-Dihydro-2,3-dimethyl-4-(2-pyridinyl)-3H-1,3-benzodiazepine hemihydrate

A solution of 8.00 g of 2-amino-N-methyl-α-(2-pyridinyl)benzeneethanamine and 36 ml of triethyl orthoacetate was treated with glacial acetic acid (12 ml). After refluxing for eight hours, the volatile components were removed at 70° C. on a rotary evaporator. The residual oil was decanted into an ice-water mixture and basified with 10% sodium hydroxide solution. The aqueous mixture was extracted with dichloromethane, dried over anhydrous magnesium sulfate and concentrated to an oil.

Purification was accomplished by preparative HPLC (Water's Associates Prep LC/System, silica gel, eluted with 2% triethylamine in methanol). Concentration of the appropriate fractions afforded an oil which solidified on standing. The solid was recrystallized from acetonitrile to yield 2.19 g of 4,5-dihydro-2,3-dimethyl- 4-(2-pyridinyl)-3H-1,3-benzodiazepine hemihydrate, mp 123°-125° C.

ANALYSIS: Calculated for $C_{16}H_{17}N_3 \cdot 0.5H_2O$: 73.90%C; 6.97%H; Found: 74.38%C; 6.93%N.

EXAMPLE 23

4,5-Dihydro-2-ethyl-3-methyl-4-(2-pyridinyl)-3H-1,3-benzodiazepine dihydrochloride monohydrate A solution of 5.0 g of 2-amino-N-methyl-α-pyridinyl)benzeneethanamine and 13.3 ml of triethyl orthoproprionate was treated with 8 ml of glacial acetic acid. After refluxing for eight hours, the volatile components were removed at 70° C. on a rotary evaporator. The residual oil was decanted into an ice-water mixture and basified with 10% sodium hydroxide solution. The aqueous mixture was extracted with dichloromethane, and the organic phase was filtered, dried over anhydrous magnesium sulfate, and concentrated to an oil.

Purification was accomplished by preparative HPLC (Water's Associates Prep LC/System 500, silica gel, elution with 2% triethylamine in methanol). Concentration of the appropriate fractions afforded 4,5-dihydro-2-ethyl-3-methyl-4-(2-pyridinyl)-3H-1,3-benzodiazepine as an oil. The oil was dissolved in methanol and treated with ethereal hydrogen chloride. Dilution with diethyl ether precipitated the corresponding hydrochloride salt. The salt was collected and dried in vacuo to yield 3.18 g of 4,5-dihydro-2-ethyl-3-methyl-4-(2-pyridinyl)-3H-1,3-benzodiazepine dihydrochloride monohydrate, mp 235°-240° C.

ANALYSIS: Calculated for $C_{17}H_{19}N_3 \cdot 2HCl \cdot H_2O$: 57.28%C; 6.50%H; 11.79%N; Found: 57.72%C; 6.32%H; 11.79%N.

EXAMPLE 24

4,5-Dihydro-3-methyl-2-phenyl-4-(2-pyridinyl)-3H-1,3-benzodiazepine dihydrochloride hydrate (4:1)

A solution of 3.5 g of 2-amino-N-methyl-α-2-pyridinyl)benzeneethanamine and 14 ml of trimethyl orthobenzoate was treated with 8 ml of glacial acetic acid. After refluxing for eight hours, the volatile components were removed at 70° C. on a rotary evaporator. The residual oil was decanted into an ice-water mixture and basified with 10% sodium hydroxide solution. The aqueous mixture was extracted with dichloromethane and the organic phase was dried over anhydrous magnesium sulfate, filtered, and concentrated to an oil.

Purification was accomplished by preparative HPLC (Water's Associates Prep LC/System 500, silica gel, elution with 2% triethylamine in methanol). Concentration of the appropriate fractions afforded an oil which was dissolved in methanol and treated with ethereal hydrogen chloride. Dilution with diethyl ether precipitated the hydrochloride salt. The salt was collected by vacuum filtration and dried in vacuo to yield 1.42 g of 4,5-dihydro-3-methyl-2-phenyl-4-(2-pyridinyl)-3H-1,3-benzodiazepine dihydrochloride hydrate (4:1), mp 244°-247° C.

ANALYSIS: Calculated for $C_{21}H_{19}N_3 \cdot 2HCl \cdot 0.25 H_2O$: 64.51%C; 5.54%H; 10.75%N; Found: 64.46%C; 5.64%H; 10.50%N.

EXAMPLE 25

N-Acetyl-2-amino-N-methyl-α-(2-pyridinyl)benzeneethanamine

A solution of 4.5 g of 2-amino-N-methyl-α-2-pyridinyl)benzeneethanamine in 60 ml of potassium hydroxide dried pyridine was thoroughly chilled and treated dropwise with 3.0 ml of acetic anhydride. After stirring overnight at room temperature, the reaction mixture was basified with 10% sodium hydroxide solution and extracted with dichloromethane. The organic phase was dried over magnesium sulfate, vacuum filtered, and concentrated to an oil, which solidified on standing.

The solid was recrystallized from acetonitrile and dried for 6 hours at 60° C. under vacuum to yield 2.96 g of N-acetyl-2-amino-N-methyl-α-(2-pyridinyl)benzeneethanamine, mp 103°-107° C.

ANALYSIS: Calculated for $C_{16}H_{19}N_3O$: 71.34%C; 7.11%H; 15.60%N; Found: 71.01%C; 7.03%H; 15.42%N.

EXAMPLE 26

N-[2-[2-(N-Acetyl-N-methyl)amino-2-(2-pyridinyl)ethyl]phenyl]acetamide

A chilled solution of 4.5 g of 2-amino-N-methyl-α-(2-pyridinyl)benzeneethanamine in 60 ml of potassium hydroxide dried pyridine was treated dropwise with 6 ml of acetic anhydride. After stirring overnight at room temperature, the reaction mixture was basified with 10% sodium hydroxide solution and extracted with dichloromethane. The organic phase was dried over anhydrous magnesium sulfate, vacuum filtered, and concentrated to a solid. The solid was recrystallized from acetonitrile and dried for 6 hours at 60° C. under vacuum to yield 3.52 g of N-[2-[2-(N-acetyl-N-methyl)amino-2-(2-pyridinyl)ethyl]phenyl]acetamide, mp 121°-124° C.

ANALYSIS: Calculated for $C_{18}H_{21}N_3O_2$: 69.43%C; 6.80%H; 13.50%N; Found: 69.33%C; 6.76%H; 13.50%N.

EXAMPLE 27

N-[2-[2-(Methylamino)-2-(3-pyridinyl)ethyl]phenyl]-2,2-dimethylpropanamide

A stirred, chilled (−5° C.) solution of 57.38 g of N-(2-methylphenyl)-2,2-dimethylpropanamide and 600 ml of tetrahydrofuran was treated dropwise over 1.25 hour with 264 ml of 2.5M n-butyllithium in hexane during which time the temperature did not exceed +3° C. (dry nitrogen atmosphere). The resultant solution was stirred for 35 min. with cooling and was then treated dropwise over 30 min. with a solution of 39.21 g of 3-pyridinecarboxaldehyde methylimine and 90 ml of toluene (temperature maintained below +3° C.). After stirring at 0° C. for 15 min. the solution was quenched by the addition of water (200 ml) and concentrated. The residue was extracted with dichoromethane (2×200 ml). The combined organic phase was dried over anhydrous sodium sulfate, filtered, and concentrated to an oil (117.4 g).

Purification was accomplished by preparative HPLC (Water's Associates Prep LC/System 500A, silica gel, sample applied in dichloromethane, eluted with methanol). Concentration of the appropriate fractions yielded an oil. A solution of the oil and diethyl ether was filtered, and the filtrate was concentrated to give 14.6 g of crude product. The crude product was purified by preparative HPLC (sample applied to the silica gel columns in 25 ml of dichloromethane, eluted first with ethyl acetate followed by elution with 10% methanol in dichloromethane). The appropriate fractions were combined and concentrated to an oil (10.6 g) which crystallized on trituration with hexane. The solid was isolated, washed with hexane, and dried in vacuo at ambient temperature to afford 9.24 g of N-[2-[2-(methylamino)-2-(3-pyridinyl)ethyl]phenyl]-2,2-dimethylpropanamide, mp 91.5°-96° C.

ANALYSIS: Calculated for $C_{19}H_{25}N_3O$: 73.28%C; 8.09%H; Found: 72.75%C; 7.94%H.

EXAMPLE 28

2-Amino-N-methyl-α-(3-pyridinyl)benzeneethanamine

A stirred solution of 7.13 g of N-[2-[2-(methylamino)-2-(3-pyridinyl)ethyl]phenyl]-2,2-dimethylpropanamide in 90 ml of 6N hydrochloric acid was refluxed for 5.5 hours and then allowed to stand overnight at room temperature. The solution was decanted over crushed ice, diluted with water (200 ml) and basified with 50% sodium hydroxide solution. The mixture was extracted with dichloromethane (3×150 ml) and the combined, organic phase was dried over anhydrous sodium sulfate, filtered, and concentrated to an oil. The oil was purified by preparative HPLC (Water's Associates Prep LC/System 500 A, silica gel, sample applied in dichloromethane, eluted with 2% triethylamine in methanol). Concentration of the appropriate fractions yielded 4.69 g of 2-amino-N-methyl-α-(3-pyridinyl)benzeneethanamine as an oil.

ANALYSIS: Calculated for $C_{14}H_{17}N_3$: 73.98%C; 7.54%H; Found: 73.82%C; 7.49%H.

EXAMPLE 29

4,5-Dihydro-2-ethyl-3-methyl-4-(3-pyridinyl)-3H-1,3-benzodiazepine

A stirred solution of 4.47 g of 2-amino-N-methyl-α-(3-pyridinyl)benzeneethanamine and 20.8 g of triethyl orthopropionate was treated rapidly with glacial acetic acid (4.4 ml). After refluxing for 7 hours with exclusion of moisture, the solution was concentrated on a rotary evaporator. The residual syrup was dissolved in 10% hydrochloric acid (100 ml) and the solution was extracted with diethyl ether (2×100 ml). The aqueous phase was basified with 10% sodium hydroxide solution and the turbid mixture was extracted with dichloromethane (2×100 ml). The organic phase was dried over anhydrous sodium sulfate, filtered, and concentrated to an oil.

Purification was accomplished by preparative HPLC (silica gel, sample applied in dichloromethane, eluted with 2% triethylamine in methanol). Concentration of the appropriate fractions and trituration with hexane afforded 2.51 g of 4,5-dihydro-2-ethyl-3-methyl-4-(3-pyridinyl)-3H-1,3-benzodiazepine, mp 72°-75° C.

ANALYSIS: Calculated for $C_{17}H_{19}N_3$: 76.95%C; 7.22%H; Found: 77.16%C; 7.22%H.

EXAMPLE 30

4,5-Dihydro-2,3-dimethyl-4-(3-pyridinyl)-3-1,3-benzodiazepine

A stirred solution of 2.5 g of 2-amino-N-methyl-α-(3-pyridinyl)benzeneethanamine and 10.71 g of triethyl orthoacetate was treated with 2.5 ml of glacial acetic acid. After refluxing for eight hours, the volatile components were removed at 70° C. on a rotary evaporator. The residual syrup was dissolved in 10% hydrochloric acid (120 ml) and the solution was extracted with ether. The aqueous phase was basified with 10% sodium hydroxide solution and extracted with dichloromethane (2×70 ml). The combined organic phase was dried over anhydrous sodium sulfate, filtered, and concentrated to an oil.

Purification was accomplished by HPLC (Water's Associates Prep LC/System 500A, silica gel, oil applied in dichloromethane, eluted with 2% triethylamine in methanol). Concentration of the appropriate fractions yielded an oil which was dissolved in diethyl ether, filtered to remove a trace of insoluble material, and concentrated until most of the ether was removed. The residual oil was seeded with crystals obtained from a previous synthesis and dried in vacuo to give 1.32 g of 4,5-dihydro-2,3-dimethyl-4-(3-pyridinyl)-3H-1,3-benzodiazepine, mp 145°-148° C.

ANALYSIS: Calculated for $C_{16}H_{17}N_3$: 76.46%C; 6.82%H; Found: 76.37%C; 6.78%H.

EXAMPLE 31

2-[2-(Methylamino-2-(4-pyridinyl)ethyl]phenyl]-2,2-dimethylpropanamide

A chilled solution (−5° C.) of 95.65 g of 2,2-dimethyl-N-[2-[2-(methylamino)-2-(4-pyridinyl)ethyl]phenyl]-propanamide in 800 ml of tetrahydrofuran was treated dropwise over 2 hours with 440 ml of a 2.5M solution of n-butyllithium in hexanes. After the addition was complete, the resultant solution was stirred for 2 hours with cooling, and then was treated dropwise over 20 min. with a solution of 71.0 g of 4-pyridine carboxaldehyde methylimine. The solution was stirred for an additional 20 minutes, quenched by the addition of water (350 ml), and concentrated. The residue was extracted with dichloromethane. The organic phase was dried over anhydrous magnesium sulfate, filtered, and concentrated to an oil.

Purification was accomplished by preparative HPLC (Water's Associates Prep LC/system 500A, silica gel, eluted with ethyl acetate). Concentration of the appropriate fractions yielded an oil which was further purified by preparative HPLC until free of impurities, triturated with hexane, and dried under vacuum to yield 2-[2-[methylamino-2-(4-pyridinyl)ethyl]phenyl]-2,2-dimethylpropanamide, mp 114°-116° C.

ANALYSIS: Calculated for $C_{19}H_{25}N_3O$: 73.28%C; 8.09%H; 13.49%N; Found: 73.18%C; 8.33%H; 13.77%N.

EXAMPLE 32

2-Amino-N-methyl-α-(4-pyridinyl)benzeneethanamine

A solution of 25 g of N-[2-[2-(methylamino-2-(4-pyridinyl)ethyl]phenyl]-2,2-dimethylpropanamide in 6N hydrochloric acid (260 ml) was refluxed for 8 hours. The solution was then decanted into an ice-water mixture (800 ml), basified with 50% sodium hydroxide solution, and the mixture extracted with dichloromethane (2000 ml). The extract was dried over anhydrous magnesium sulfate and concentrated to an oil which solidified upon standing.

Purification was accomplished by preparative HPLC (Water's Associates Prep LC/System 500A, silica gel, eluted with methanol). Concentration of the appropriate fractions yielded a solid which was triturated with hexane and dried overnight in vacuo at ambient temperature to yield 13.52 g of 2-amino-N-methyl-α-(4-pyridinyl)benzeneethanamine, mp 69°-71° C.

ANALYSIS: Calculated for $C_{14}H_{17}N_3$: 73.98%C; 7.54%H; Found: 73.97%C; 7.54%H.

EXAMPLE 33

4,5-Dihydro-2,3-dimethyl-4-(4-pyridinyl)-3H-1,3-benzodiazepine

A solution of 4.0 g of 2-amino-N-methyl-α-(4-pyridinyl)-benzeneethanamine and 18 ml of triethyl orthoacetate was treated with glacial acetic acid (6 ml). After refluxing for 8 hours, the volatile components were removed at 70° C. on a rotary evaporator. The residual oil was decanted into an ice-water mixture, basified with 10% sodium hydroxide solution, extracted with dichloromethane, dried over anhydrous magnesium sulfate, and concentrated to an oil.

Purification was accomplished by preparative HPLC (Water's Associates Prep LC/System 500, silica gel, eluted with triethylamine in methanol). The appropriate fractions were combined and concentrated to an oil which solidified upon standing. The solid was recrystallized from acetonitrile (10 ml) to yield 2.18 g of 4,5-dihydro-2,3-dimethyl-4-(4-pyridinyl)-3H-1,3-benzodiazepine, mp 159°-161° C.

ANALYSIS: Calculated for $C_{16}H_{17}N_3$: 76.46%C; 6.82%H; Found: 76.50%C; 6.59%H.

EXAMPLE 34

4,5-Dihydro-2-ethyl-3-methyl-4-(4-pyridinyl)-3H-1,3-benzodiazepine hemihydrate A solution of 5.00 g of 2-amino-N-methyl-α-(4-pyridinyl)benzeneethanamine and triethyl orthopropionate (24.33 ml) was treated with glacial acetic acid (7.34 ml). After refluxing for 8 hours, volatile components were removed at 40° C. on a rotary evaporator. The residual oil was acidified with 10% hydrochloric acid aqueous solution (75 ml) and extracted with diethyl ether (3×100 ml). The aqueous phase was basified with 10% sodium hydroxide solution and extracted with dichloromethane (3×100 ml). The combined dichloromethane layers were washed with water (100 ml), dried over anhydrous sodium sulfate and concentrated on a rotary evaporator to an oil.

Purification was accomplished by preparative HPLC (Water's Associates Prep LC/System 500A; silica gel; eluted with 2% triethylamine in methanol). Concentration of the appropriate fractions afforded an oil, which solidified upon refrigeration. The solid was triturated with ether, and dried in vacuo to afford 2.98 g of 4,5-dihydro-2-ethyl-3-methyl-4-(4-pyridinyl)-3H-1,3-benzodiazepine hemihydrate, mp 58°-68° C.

ANALYSIS: Calculated for $C_{17}H_{19}N_3 \cdot 0.5H_2O$: 74.42%C; 7.35%H; 15.32%N; Found: 75.22%C; 7.22%H; 15.43%N.

EXAMPLE 35

4,5-Dihydro-3-methyl-4-(3-methyl-2-thienyl)-2-(1-propyl)-3H-1,3-benzodiazepine hydrochloride monohydrate A solution of 5.0 g of 2-amino-N-methyl-α-(3-methyl-2-thienyl)benzeneethanamine, 18.02 ml trimethyl orthobutyrate and 6.8 ml of glacial acetic acid was refluxed for 8 hours under a nitrogen atmosphere. The solution was concentrated at 40° C. on a rotary evaporator and the residual oil was acidified with 10% hydrochloric acid solution (60 ml) and extracted with diethyl ether (3×70 ml). The acidic aqueous phase was basified with 10% sodium hydroxide solution (100 ml) and extracted with diethyl ether (3×100 ml). The ethereal phase was dried over sodium sulfate/magnesium sulfate, filtered and concentrated to an oil. Purification was accomplished by HPLC (Water's Associates Prep LC/System 500A, silica gel, utilizing methanol followed by 2% triethylamine in methanol as successive eluents). Concentration of the appropriate fractions yielded 4,5-dihydro-3-methyl-4-(3-methyl-2-thienyl)-2-(1-propyl)-3H-1,3-benzodiazepine as an oil.

The oil was treated with ethereal hydrogen chloride, and the resultant precipitate triturated with ethyl acetate to afford 2.93 g of 4,5-dihydro-3-methyl-4-(3-methyl-2-thienyl)-2-(1-propyl)-3H-1,3-benzodiazepine hydrochloride monohydrate, mp 181.5°-182.0° C.

ANALYSIS: Calculated for $C_{18}H_{22}N_2S \cdot HCl \cdot H_2O$: 61.25%C; 6.57%H; 7.94%N; Found: 61.60%C; 6.96%H; 8.41%N.

EXAMPLE 36

(a)

2-Amino-5-bromo-N-methyl-α-(3-methyl-2-thienyl)-benzeneethaneamine

A stirred solution of 5.02 g of 2-amino-N-methyl-α-(3-methyl-2-thienyl)benzeneethanamine and 79 ml of dimethylformamide was treated with a solution of 4.71 g N-bromosuccinimide in 55 ml of dimethylformamide. The solution was stirred for 8 h with the exclusion of moisture and then concentrated to an oil on a rotary evaporator (70° C.) under high vacuum. The oil was diluted with distilled water (100 ml) and basified with a 10% sodium hydroxide solution (25 ml). The basic solution was extracted with dichloromethane (3×100 ml). The organic phase was dried over anhydrous sodium sulfate, filtered and concentrated to an oil. Thin layer chromatography (silica gel, methanol eluent) indicated a 2-component mixture.

Purification was accomplished by preparative HPLC (Water's Associates Prep LC/System 500, silica gel, utilizing methanol as the eluent). Concentration of the slower eluting fractions yielded an oil which was dissolved in diethyl ether and allowed to crystallize. The resulting precipitate was collected and dried to afford 2.6 g of 2-amino-5-bromo-N-methyl-(3-methyl-2-thienyl)benzeneethanamine, mp 68°-70° C.

ANALYSIS: Calculated for $C_{14}H_{17}BrN_2S$: 51.70%C; 5.27%H; 8.61%N; Found: 52.11%C; 5.18%H; 8.43%N.

(b)

2-Amino-3,5-dibromo-N-methyl-α-(3-methyl-2-thienyl)benzeneethanamine dihydrochloride The faster eluting fractions obtained from the HPLC separation described supra were concentrated to an oil which was dissolved in diethyl ether, filtered free of insoluble material and concentrated. Trituration of the resultant oil with hexane afforded 2-amino-3,5-dibromo-N-methyl-α-(3-methyl-2-thienyl) benzeneethanamine as a solid. The solid was dissolved in methanol and treated with ethereal hydrogen chloride. Dilution with diethyl ether precipitated 0.9 g of the corresponding dihydrochloride salt, mp 141°-143° C.

ANALYSIS: Calculated for $C_{14}H_{16}Br_2N_2S \cdot 2HCl$: 35.25%C; 3.80%H; 5.87%N; Found: 35.55%C; 3.89%H; 5.51%N.

EXAMPLE 37

N-[2-[2-(Methylamino)-2-(5-methyl-2-thienyl)ethyl]-phenyl]-2,2-dimethylpropanamide hydrochloride hemihydrate A stirred, chilled (5° C.) solution of 60 g of 2,2-dimethyl-N-[(2-methyl)phenyl]propanamide and 470 ml of tetrahydrofuran was treated over one hour with 284 ml of a 2.5M solution of n-butyllithium in hexane (nitrogen atmosphere). The solution was stirred for 45 min at 0° C. and the resultant suspension was then treated over one hour with a solution of 52.41 g of 5-methyl-2-thiophenecarboxaldehyde methylimine in 470 ml of tetrahydrofuran (temperature maintained below 10° C.). After stirring the mixture at room temperature for 45 minutes, 225 ml of water was added to quench the reaction. The mixture was concentrated on a rotary evaporator and the aqueous residue was extracted with diethyl ether (3×100 ml). The combined organic phase was dried over anhydrous sodium sulfate and magnesium sulfate, filtered, and concentrated to yield 114 g of N-[2-[2-(methylamino)-2-(5-methyl-2-thienyl)ethyl)]phenyl]-2,2-dimethyl propanamide as an oil.

A 10 g aliquot of the oil was purified by preparative HPLC (Water's Associates Prep LC/System 500A, silica gel, sample applied in dichloromethane, eluted with 25% acetone in hexane). A solution of the oil and methanol was treated with a slight excess of ethereal hydrogen chloride and then diluted with diethyl ether to yield N-[2-[2-(methylamino)-2-(5-methyl-2-thienyl)-ethyl]phenyl]-2,2-dimethylpropanamide hydrochloride hemihydrate (3.0 g), mp 91°-101° C.

ANALYSIS: Calculated for $C_{19}H_{26}N_2O \cdot HCl \cdot 0.5-H_2O$: 60.70%C; 7.51%H; 7.45%N; Found: 60.55%C; 7.45%H; 7.34%N.

EXAMPLE 38

2-Amino-N-methyl-α-(5-methyl-2-thienyl)benzeneethanamine

A solution of 22.73 g of N-[2-[2-(methylamino)-2-(5-methyl-2-thienyl)ethyl]phenyl]-2,2-dimethylpropanamide and 100 ml of 6N hydrochloric acid solution was refluxed for eight hours. The solution was decanted over 200 ml of ice and basified with 70 ml of a 50% sodium hydroxide solution. The aqueous mixture was extracted with dichloromethane and the organic phase was dried over anhydrous sodium sulfate, filtered, and concentrated to an oil.

Purification was accomplished by preparative HPLC (Water's Associates Prep LC/System 500, silica gel, eluted with methanol). Concentration of the appropriate fractions afforded an oil which was dissolved in 100 ml of diethyl ether, filtered to remove any insoluble impurities, and concentrated to yield 10.77 g of 2-amino-N-methyl-α-(5-methyl-2-thienyl)benzeneethanamine as an oil.

ANALYSIS: Calculated for $C_{14}H_{18}N_2S$: 68.25%C; 7.36%H; 11.37%N; Found: 68.07%; 7.20%H; 11.14%N.

EXAMPLE 39

4,5-Dihydro-2,3-dimethyl-4-(5-methyl-2-thienyl)-3H-1,3-benzodiazepine

A stirred solution of 7.1 g of 2-amino-N-methyl-(5-methyl-2-thienyl)benzeneethanamine and 31.6 ml of triethyl orthoacetate was treated with 6.9 ml of glacial acetic acid. After refluxing for 8 hours the solution was concentrated at 70° C. on a rotary evaporator. The resulting oil was washed with 10% hydrochloric acid solution (120 ml), followed by ether (2×100 ml). The aqueous phase was basified with a 10% sodium hydroxide solution (120 ml) and extracted with dichloromethane (3×100 ml). The combined organic phase was dried over anhydrous sodium sulfate, filtered and concentrated. The concentrate was purified by preparative HPLC (Water's Associates Prep LC/System 500, silica gel, eluted with 2% triethylamine in methanol). Concentration of the appropriate fractions yielded an oil. The oil was dissolved in diethyl ether and filtered to remove insoluble impurities. Concentration of the filtrate yielded 3.15 g of 4,5-dihydro-2,3-dimethyl-4-(5-methyl-2-thienyl)-3H-1,3-benzodiazepine, mp 139°-140° C.

ANALYSIS: Calculated for $C_{16}H_{18}N_2S$: 71.07%C; 6.71%H; 10.36%N; Found: 71.06%C; 6.80%; 10.22%N.

EXAMPLE 40

4,5-Dihydro-2-ethyl-3-methyl-4-(5-methyl-2-thienyl)-3H-1,3-benzodiazepine

A stirred solution of 5.88 g of 2-amino-N-methyl-α-(5-methyl-2-thienyl)benzeneethanamine and 29 ml of triethyl orthopropionate was treated with 5.5 ml of glacial acetic acid. After refluxing for 8 hours, the solution was concentrated to an oil at 70° C. on a rotary evaporator. The oil was washed with a 10% hydrochloric acid solution (100 ml) and water was added to dissolve observed solids. The aqueous phase was washed with diethyl ether (2×50 ml) and then basified with a 10% sodium hydroxide solution (100 ml). The mixture was extracted with dichloromethane (3×100 ml) and the combined organic phase was dried over anhydrous sodium sulfate, filtered, and concentrated.

Purification was accomplished by preparative HPLC (Waters Associates Prep LC/System 500, silica gel, 2% triethylamine in methanol as the eluent). Concentration of the appropriate fractions yielded an oil which was dissolved in ether and filtered to remove all traces of insoluble material. The filtrate was concentrated to an oil, which was triturated with hexane to afford 1.51 g of 4,5-dihydro-2-ethyl-3-methyl-4-(5-methyl-2-thienyl)-3H-1,3-benzodiazepine as a solid, mp 66° C.

ANALYSIS: Calculated for $C_{17}H_{20}N_2S$: 71.79%C; 7.09%H; 9.85%N; Found: 71.74%C; 7.21%H; 9.90%N.

EXAMPLE 41

2-[(2,5-Dioxo-1-pyrrolidinyl)methyl]amino-N-formyl-N-methyl-α-(3-methyl-2-thienyl)benzeneethanamine A stirred solution of 8 g of 2-amino-N-formyl-N-methyl-α-(3-methyl-2-thienyl)benzeneethanamine in 30 ml of 95% ethanol was treated with 2.4 ml of a 37% formaldehyde solution and 3.6 g of succinimide. The solution was heated for 6 hours at 98° C. and then allowed to stand at ambient temperature for 24 hours. The resulting precipitate was filtered, washed (95% ethanol; 3×50 ml), and dried in vacuo (40° C.) to afford 7.62 g of 2-[(2,5-dioxo-1-pyrrolidinyl)methyl]amino-N-formyl-N-methyl-α-(3-methyl-2-thienyl)benzeneethanamine, mp 160°-164° C.

ANALYSIS: Calculated for $C_{20}H_{23}N_3O_3S$: 62.30%C; 6.01%H; 10.90%N; Found: 62.09%C; 5.98%H; 10.82%N;

EXAMPLE 42

N-Formyl-N-methyl-2-methylamino-α-(3-methyl-2-thienyl)benzeneethanamine hydrochloride monohydrate A mixture of 6.39 g of 2-[(2,5-dioxo-1-pyrrolidinyl)methyl]amino-N-formyl-N-methyl-α-(3-methyl-2-thienyl)benzeneethanamine, 20 ml of anhydrous dimethyl sulfoxide and 0.72 g of sodium borohydride was stirred at ambient temperature for 15 minutes and then heated on a steam bath for 15 minutes with occasional agitation. After standing for 2 hours at ambient temperature, the reaction mixture was decanted into 150 ml of water and extracted with diethyl ether (2×100 ml). The organic phase was washed with water (2×100 ml), dried over anhydrous sodium sulfate, and concentrated to an oil. Thin layer chromatography of the resultant oil indicated a multi-component mixture. Purification of the mixture was accomplished by HPLC (Waters Associates Prep LC/System 500, silica gel, elution with methanol]. Concentration of the appropriate fractions afforded N-formyl-N-methyl-2-methylamino-α-(3-methyl-2-thienyl)benzeneethanamine) as an oil.

A solution of the oil and diethyl ether was treated with ethereal hydrogen chloride to precipitate the corresponding hydrochloride salt. The precipitate was dried in vacuo to yield 1.7 g of N-formyl-N-methyl-2-methylamino-α-(3-methyl-2-thienyl)benzeneethanamine hydrochloride monohydrate, mp 140°–145° C.

ANALYSIS: Calculated for $C_{16}H_{20}N_2OS \cdot HCl \cdot H_2O$: 56.05%C; 6.76%H; 8.17%N; Found: 56.00%C; 6.79%H; 7.85%N.

EXAMPLE 43

2-Amino-5-chloro-N-methyl-α-(3-methyl-2-thienyl)-benzeneethanamine

A stirred solution of 8 g of 2-amino-N-methyl-α-(3-methyl-2-thienyl)benzeneethanamine in 40 ml of N,N-dimethylformamide was treated with a solution of 6.41 g of N-chlorosuccinimide in 40 ml of N,N-dimethylformamide and then stirred at room temperature for 8 hours. Evaporation of the volatiles afforded an oil which was decanted into 100 ml of water, basified with 30 ml of 10% aqueous sodium hydroxide and extracted with dichloromethane (2×100 ml). The extract was washed with water (2×100 ml), dried over anhydrous sodium sulfate and concentrated. Thin layer chromatography of the resultant oil indicated a multicomponent mixture. Purification of the mixture was accomplished by successive HPLC separations (Water's Associates Prep LC/System 500, silica gel, elution with methanol). Concentration of the appropriate fractions afforded a residue which was dissolved in diethyl ether, filtered free of insolubles and concentrated. The resultant oil crystallized upon standing to yield 1.05 g of 2-amino-5-chloro-N-methyl-α-(3-methyl-2-thienyl)benzeneethanamine, mp 59°–61° C.

ANALYSIS: Calculated for $C_{14}H_{17}ClN_2S$: 59.89%C; 6.10%H; 9.97%N; Found: 60.24%C; 6.10%H; 9.99%N.

EXAMPLE 44

N-[2-(2-(methylamino)-2-(2-methyl-3-thienyl)ethyl)-phenyl]-2,2-dimethylpropanamide A chilled solution (−2° C.) of 37.9 g of 2,2-dimethyl-N-[(2-methyl)phenyl]propanamide in 350 ml of tetrahydrofuran was treated dropwise over 2 hours with 180 ml of 2.5 m n-butyllithium in hexane, and then stirred for 45 minutes with cooling. The resultant suspension was treated dropwise over 15 minutes with a solution of 13.6 g of 2-methyl-3-thiophenecarboxaldehyde methylimine in 40 ml of tetrahydrofuran. The reaction mixture was stirred for 1 hour, quenched by the addition of 17.4 ml of methanol and 200 ml of water, and concentrated. The concentrate was extracted with dichloromethane and the combined extract was dried over anhydrous sodium sulfate, filtered, and evaporated to an oil. Preliminary purification of the oil was achieved by HPLC separation (Water's Associates Prep LC/System 500, silica, elution with 20% methanol in ethyl acetate). Concentration of the appropriate fractions afforded an oil which was dissolved in diethyl ether and concentrated to yield 24.0 g of N-[2-(2-methylamino)-2-(2-methyl-3-thienyl)ethyl)phenyl]-2,2-dimethylpropanamide, mp 95°–96° C.

ANALYSIS: Calculated for $C_{19}H_{26}N_2OS$: 69.05%C; 7.93%H; 8.48%N; Found: 68.97%C; 7.95%H; 8.41%N.

EXAMPLE 45

2-Amino-N-methyl-α-(2-methyl-3-thienyl)benzeneethanamine dihydrochloride

A solution of 11.0 g of N-[2-(2-(methylamino)-2-(2-methyl-3-thineyl)ethyl)phenyl]-2,2-dimethylpropanamide in 300 ml of 6N hydrochloric acid was refluxed for 8 hours. The solution was then decanted into an ice-water mixture and basified with 50% aqueous sodium hydroxide solution. The aqueous mixture was extracted with dichloromethane (900 ml) and the organic phase was dried over anhydrous sodium sulfate, filtered and concentrated to yield 9.5 g of 2-amino-N-methyl-α-(2-methyl-3-thienyl)benzeneethanamine as an oil.

A 3.0 g aliquot of the oil was dissolved in 45 ml of methanol and the resultant solution was acidified to a pH of 1 with ethereal hydrogen chloride. Dilution with anhydrous diethyl ether (45 ml) precipitated the corresponding hydrochloride salt.

The precipitate was dried in vacuo (40°) over sodium hydroxide to yield 2.5 g of 2-amino-N-methyl-α-(2-methyl-3-thienyl)benzeneethanamine dihydrochloride, mp 229°–230° C.

ANALYSIS: Calculated for $C_{14}H_{18}N_2S \cdot 2HCl$: 52.66%C; 6.31%H; 8.78%N; Found: 52.40%C; 6.29%H; 8.59%N.

EXAMPLE 46

N-Acetyl-2-amino-N-methyl-α-(3-methyl-2-thienyl)-benzeneethanamine

A stirred, ice water chilled solution of 5.07 g of 2-amino-N-methyl-α-(3-methyl-2-thienyl)benzeneethanamine in 40 ml of pyridine was treated dropwise with 2.25 g of acetic anhydride. The solution was stirred with cooling for 15 minutes and then at room temperature for 3 hours. After standing overnight, the reaction mixture was decanted into water (200 ml), treated with dichloromethane (100 ml) and basified with 10% sodium hydroxide solution. The aqueous phase was extacted with dichloromethane (150 ml), and the combined organic phase was filtered and concentrated. The resulting solid was stirred with toluene and evaporated to dryness. Recrystallization from propionitrile (14 ml) afforded 3.0 g of N-acetyl-2-amino-N-methyl-α-(3-methyl-2-thienyl)benzeneethanamine, mp 176°–181.5° C.

ANALYSIS: Calculated for $C_{16}H_{20}N_2OS$: 66.63%C; 6.99%H; 9.71%N; Found: 66.82%C; 7.00%H; 9.73%N.

EXAMPLE 47

(a)

2-Amino-N-formyl-N-methyl-α-(3-methyl-2-thienyl)-benzeneethanamine

A stirred solution of 5.00 g of 2-amino-N-methyl-α-(3-methyl-2-thienyl)benzeneethanamine and 235 ml of ethyl formate was refluxed for 8 hours. Volatile components were removed at 60° C. on a rotary evaporator. Thin layer chromatography (silica gel, ethyl acetate as the eluent) of the resultant oil indicated a multi-component mixture. HPLC of the mixture (Water's Associates Prep LC/System 500, silica gel, elution with ethyl acetate) permitted component separation. The faster eluting fractions were concentrated to an oil which crystallized upon standing. Recrystallization from methanol-water afforded 1.2 g of 2-amino-N-formyl-N-methyl-α-(3-methyl-2-thienyl)benzeneethanamine, mp 111°–112° C.

ANALYSIS: Calculated for $C_{15}H_{18}N_2OS$: 65.66%C; 6.61%H; 10.21%N; Found: 65.46%C; 6.66%H; 10.26%N.

(b)

N-[2-[2-(N-Formyl-N-methyl)amino-2-(3-methyl-2-thienyl)ethyl]phenylformamide

Concentration of the more slowly eluting fractions obtained from the HPLC separation described supra afforded a residue which was dissolved in diethyl ether, filtered, and concentrated to an oil which solidified upon standing. The crystalline product was triturated in hexane, filtered, and dried in vacuo at 40° C. to afford 10 g of N-[2-[2-(N-formyl-N-methyl)amino-2-(3-methyl-2-thienyl)-ethyl]phenyl]formamide, mp 128°–130° C.

ANALYSIS: Calculated for $C_{16}H_{18}N_2O_2S$: 63.56%C; 6.00%H; 9.27%N; Found: 63.34%C; 6.06%H; 9.18%N.

EXAMPLE 48

2-Amino-N,N-dimethyl-α-(3-methyl-2-thienyl)benzeneethanamine

A stirred solution of 5.79 g of 2-amino-N-formyl-N-methyl-α-(3-methyl-2-thienyl)benzeneethanamine in 400 ml of tetrahydrofuran was treated dropwise under nitrogen with 90 ml of a 1M solution of borane in tetrahydrofuran. The solution was stirred overnight at room temperature and then quenched with 60 ml of a 10% sodium hydroxide solution. The aqueous mixture was extracted with dichloromethane (2×100 ml), dried over anhydrous sodium sulfate, filtered and concentrated. The concentrate was treated with 15 ml of glacial acetic acid and 35 ml of concentrated hydrochloric acid. After stirring at room temperature overnight, the solution was decanted over 200 g of ice, basified with 20 ml of 50% aqueous sodium hydroxide, and extracted with dichloromethane (3×100 ml). The organic phase was dried over anhydrous sodium sulfate, filtered and concentrated. Purification was accomplished by means of HPLC (Water's Associates Prep LC/System 500, silica gel, elution with methanol). Concentration of the appropriate fraction afforded a solid which was recrystallized from diethyl ether to afford 3.7 g of 2-amino-N,N-dimethyl-α-(3-methyl-2-thienyl)benzenethanamine, mp 75°–77° C.

ANALYSIS: Calculated for $C_{15}H_{20}N_2S$: 69.19%C; 7.74%H; 10.76%N; Found: 69.25%C; 7.81%H; 10.66%N.

EXAMPLE 49

2-Amino-5-bromo-N-methyl-α-(2-methyl-3-thienyl)-benzeneethanamine

A stirred solution of 3.0 g of 2-amino-N-methyl-α-(2-methyl-3-thienyl)benzeneethanamine in 50 ml of N,N-dimethylformamide was treated with a solution of 2.6 g of N-bromosuccinimide in 50 ml of N,N-dimethylformamide and allowed to stand overnight at room temperature. Evaporation of the volatiles afforded an oil which was purified by HPLC (Water's Associates Prep LC/System 500, silica gel, elution with methanol). The resultant oil was dissolved in diethyl ether, filtered and concentrated. Trituration with diethyl ether afforded 1.2 g of 2-amino-5-bromo-N-methyl-α-(2-methyl-3-thienyl)benzeneethanamine, mp 72.5°–74° C.

ANALYSIS: Calculated for $C_{14}H_{17}BrN_2S$: 51.69%C; 5.27%H; 8.61%N; Found: 52.10%C; 5.25%H; 8.57%N;

EXAMPLE 50

N-Methyl-2 methylamino-α-(3-methyl-2-thienyl)benzeneethanamine dihydrochloride

N-Formyl-N-methyl-2-methylamine-α-(3-methyl-2-thienyl)benzeneethanamine (4.1 g) was treated with 18 ml of 3N hydrochloric acid. After refluxing for 1.5 hours the solution was decanted over ice, basified with 12 ml of a 50% aqueous sodium hydroxide solution and extracted with dichloromethane (3×60 ml). The organic phase was dried over anhydrous sodium sulfate and concentrated to an oil. Purification of the oil was accomplished by HPLC (Water's Associates Prep LC/System 500, silica gel, elution with methanol). Concentration of the appropriate fractions afforded a residue which was dissolved in diethyl ether, filtered free of insolubles, and concentrated to afford N-methyl-2-methylamino-α-(3-methyl-2-thienyl)benzeneethanamine as an oil. The oil was dissolved in methanol and treated with ethereal hydrogen chloride. Dilution with diethyl ether precipitated 2.4 g of the corresponding dihydrochoride salt, mp 191°–192° C.

ANALYSIS: Calculated for $C_{15}H_{20}N_2S \cdot 2HCl$: 54.05%C; 6.65%H; 8.40%N; Found: 54.19%C; 6.64%H; 8.36%N.

EXAMPLE 51

N,N-Dimethyl-2-methylamino-α-(3-methyl-2-thienyl)-benzeneethanamine

A solution of 7.2 g of N-[2-[2-(N-formyl-N-methyl)amino-2-(3-methyl-2-thienyl)ethyl]phenyl]formamide in 600 ml of tetrahydrofuran was treated with 144 ml of a 1M borane-tetrahydrofuran complex under nitrogen at room temperature. After stirring overnight, the mixture was quenched with 10% sodium hydroxide solution, and concentrated to remove the solvent. The concentrate was extracted with dichloromethane (3×150 ml), dried over anhydrous sodium sulfate, filtered, and concentrated to an oil. The oil was dissolved in 20 ml of glacial acetic acid, and treated dropwise with 120 ml of concentrated hydrochloric acid, and left to stir at room temperature overnight. The solution was then decanted over 300 g of ice, basified with 50% sodium hydroxide solution, extracted with dichloromethane (3×200 ml), dried over anhydrous sodium sulfate, filtered and concentrated to an oil.

Purification of the oil was accomplished by preparative HPLC (Water's Associates Prep LC/System 500, silica gel, elution with methanol). The appropriate fractions were collected, combined and concentrated to give 4.6 g of N,N-dimethyl-2-methylamino-α-(3-methyl-2-thienyl)benzeneethanamine as an oil.

ANALYSIS: Calculated for $C_{16}H_{22}N_2S$: 70.03%C; 8.08%H; 10.21%N; Found: 70.13%C; 8.23%H; 10.10%N.

EXAMPLE 52

N,N-Dimethyl-2-dimethylamino-α-(3-methyl)-2-thienyl)benzeneethanamine

A solution of 5.4 g of 2-amino-N-methyl-α-(3-methyl-2-thienyl)benzeneethanamine in 50 ml of acetonitrile and 11.5 ml of a 37% (w/w) formaldehyde solution was treated with 3.1 g of sodium cyanoborohydride. After stirring at room temperature for 2.5 hours, the reaction mixture was dissolved in 80 ml of diethyl ether and extracted with an aqueous potassium hydroxide solution (3×75 ml). The ethereal layer was washed with 150 ml of saturated brine, dried with anhydrous potassium carbonate, filtered and concentrated.

Purification of the resultant oil was accomplished by preparative HPLC (Water's Associates Prep LC/System 500, silica gel, elution with methanol). The appropriate fractions were collected, combined and concentrated. The concentrate was dissolved in diethyl ether, filtered and concentrated to afford 3.1 g of N,N-dimethyl-2-dimethylamino-α-(3-methyl-2-thienyl)benzeneethanamine as an oil.

ANALYSIS: Calculated for $C_{17}H_{24}N_2S$: 70.79%C; 8.40%H; 9.71%N; Found: 70.70%C; 8.41%H; 9.79%N.

EXAMPLE 53

N-Formyl-2-hydroxy-N-methyl-α-(3-methyl-2-thienyl)benzeneethanamine

A stirred suspension of 8.87 g of 2-amino-N-formyl-N-methyl-α-(3-methyl-2-thienyl)benzeneethanamine and 71 ml of 50% (w/v) sulfuric acid was chilled with an ice water bath for 15 minutes. The suspension was treated dropwise over one minute with a solution of sodium nitrite (2.45 g) and water (13 ml). After stirring with chilling for 15 minutes, the mixture was strained through glass wool into a dropping funnel and then added over a few minutes to a refluxing solution of 63.84 g of copper sulfate and 130 ml of water. After a few minutes of vigorous stirring, the reaction mixture was cooled to room temperature with an ice bath, diluted with water and dichloromethane and transferred to a separatory funnel. The phases were separated and the aqueous phase was extracted with dichloromethane (2×200 ml). The combined organic phase was dried over anhydrous sodium sulfate, filtered, and concentrated to an oil. The oil was purified by means of preparative HPLC (Water's Associates Prep LC/System 500, silica gel, sample applied in dichloromethane and eluted with ethyl acetate-hexane (1:1)). The appropriate fractions were combined and concentrated to an oil which crystallized on refrigerated storage overnight. Recrystallization from ethyl acetate (20 ml) afforded 1.62 g of N-formyl-2-hydroxy-N-methyl-α-(3-methyl-2-thienyl)-benzeneethanamine, mp 142°–144° C.

ANALYSIS: Calculated for $C_{15}H_{17}NO_2S$: 65.43%C; 6.22%H; 5.09%N; Found: 65.37%C; 6.20%H; 5.00%N.

EXAMPLE 54

2-Hydroxy-N-methyl-α-(3-methyl-2-thienyl)benzeneethanamine hydrochloride

A stirred suspension of 4.0 g of N-formyl-2-hydroxy-N-methyl-α-(3-methyl-2-thienyl)benzeneethanamine and 40 ml of methanol was treated with 40 ml of 3N hydrochloric acid to afford a turbid yellow mixture. After heating to reflux, sufficient methanol (40 ml) was added to give a yellow solution. After refluxing for 5 hours, the solution was concentrated on a rotary evaporator to remove the methanol. The residual oil-water mixture was diluted with dichloromethane and basified with 5% sodium bicarbonate solution. The phases were separated and the aqueous phase was extracted with dichloromethane (2×100 ml). The combined organic phase was dried over sodium sulfate and concentrated to an oil which was shown to be a three component mixture by thin layer analysis.

The oil was purified by preparative HPLC (Water's Associates Prep LC/System 500, silica gel, sample applied in dichloromethane (20 ml), elution with methanol-ethyl acetate dicholoromethane). Concentration of the appropriate fractions afforded an oil, which was repurified by preparative HPLC to remove a trace of the starting amide. Concentration of the appropriate fractions gave 2.35 g of 2-hydroxy-N-methyl-α-(3-methyl-2-thienyl)benzeneethanamine as an oil. The oil was dissolved in anhydrous ether and the solution was treated with ethereal hydrogen chloride to give a precipitate, which was collected and dried in vacuo at 40° C., over sodium hydroxide pellets. Recrystallization from absolute ethanol (20 ml) by gradual dilution with diethyl ether gave 1.54 g (37%) of 2-hydroxy-N-methyl-α-(3-methyl-2-thienyl)benzeneethanamine hydrochloride, mp 195.5°–196.5° C.

ANALYSIS: Calculated for $C_{14}H_{17}NOS \cdot HCl$: 59.25%C; 6.39%H; 4.94%N; Found: 59.24%C; 6.38%H; 4.88%N;

EXAMPLE 55

4,5-Dihydro-2-ethyl-3-methyl-4-(2-methyl-3-thienyl)-3H-1,3-benzodiazepine

A solution of 3.95 g of 2-amino-N-methyl-α-(2-methyl-3-thienyl)benzeneethanamine, 5 ml of glacial acetic acid and 17.0 g of triethylorthopropionate was refluxed for 8 hours (under a nitrogen atmosphere). The solution was concentrated in vacuo at 80° C. and the residual oil dissolved in diethyl ether (50 ml) and acidified with 10% hydrochloric acid solution. The aqueous phase was washed with diethyl ether (50 ml), basified, and extracted with dichloromethane (2×100 ml). The combined organic phase was dried over anhydrous sodium sulfate, filtered and concentrated. The resultant oil was purified by preparative HPLC (Water's Associates Prep LC/System 500, silica gel, elution with methanol followed by 2% triethylamine in methanol). Concentration of the appropriate fractions afforded 2.26 g of 4,5-dihydro-2-ethyl-3-methyl-4-(2-methyl-3-thienyl)-3H-1,3-benzediazepine as an oil. Trituration with hexane afforded a solid which was combined with product obtained from previous run to afford the analytical sample, mp 82°–83.5° C.

ANALYSIS: Calculated for $C_{17}H_{20}N_2S$: 71.79%C; 7.09%H; 9.85%N; Found: 71.68%C; 7.19%H; 9.75%N;

EXAMPLE 56

4,5-Dihydro-2,3-dimethyl-4-(2-methyl-3-thienyl)-3H-1,3-benzodiazepine

A stirred solution of 4.0 g of 2-amino-N-methyl-α-(2-methyl-3-thienyl)benzeneethanamine, 15.8 g of triethyl orthoacetate, and 5 ml of glacial acetic acid was refluxed for 8 hrs. The mixture was evaporated, and the residue was dissolved in ether and acidified with 40 ml of 10% hydrochloric acid. The aqueous phase was washed with ether, basified with 10% sodium hydroxide solution, and extracted with dichloromethane. The combined extracts were dried over anhydrous sodium sulfate, filtered and concentrated. The residue was purified by preparative HPLC (Waters Associates Prep LC/System 500, silica gel, sample loaded in methanol, eluted with methanol followed by 2% triethylamine in methanol). The appropriate fractions were combined and evaporated. The residue was dissolved in dichloromethane and filtered. Concentration of the filtrate afforded 2.10 g of product, mp 91°–92° C.

ANALYSIS: Calculated for $C_{16}H_{18}N_2S$: 71.07%C; 6.71%H; 10.36%N; Found: 71.31%C; 6.58%H; 10.34%N;

EXAMPLE 57

8-Chloro-4,5-dihydro-2-ethyl-3-methyl-4-(3-methyl-2-thienyl)-3H-1,3-benzodiazepine A stirred solution of 3.05 g of 2-amino-4-chloro-N-methyl-α-(3-methyl-2-thienyl)benzeneethanamine, 11.63 g of triethyl orthopropionate and 3.7 ml of glacial acetic acid, was refluxed for 8 hr and then concentrated at 80° C. The residue was washed with 10% hydrochloric acid, and the aqueous phase was washed with ether, basified with 10% sodium hydroxide solution and extracted with dichloromethane. The combined organic phases were dried over anhydrous sodium sulfate, filtered and concentrated. Purification was accomplished by preparative HPLC (Water's Associates Prep LC/System 500A, silica gel, eluted with methanol, flow rate of 200 ml/min, GOW-MAC Model 80-800 UV detector). The appropriate fractions were combined and concentrated to afford a solid. The solid was dissolved in ether and filtered. The filtrate was concentrated and the residue was triturated with ether to give 1.2 g of product, mp 94°–96° C.

ANALYSIS: Calculated for $C_{17}H_{19}ClN_2S$: 64.04%C; 6.01%H; 8.79%N; Found: 63.72%C; 6.04%H; 8.62%N.

EXAMPLE 58

4-Chloro-β-(dimethylamino)-α-(3-methyl-2-thenoyl)-2-nitrosytrene

A stirred solution of 34.32 g of 4-chloro-2-nitrotoluene in 100 ml of anhydrous dimethylformamide and 28.6 g of 94% dimethylformamide dimethylacetal was heated to 128° C. and then stirred overnight with collection of a distillate. An additional 12.0 g of 94% dimethylformamide dimethylacetal was added. The solution was heated to 158° C. for 3 hr, and then concentrated.

To a stirred solution of 12.62 g of the residue in 100 ml of tetrahydrofuran and 6.07 g of triethylamine was added dropwise, 9.64 g of 3-methyl-2-thiophenecarbonyl chloride in 20 ml of tetrahydrofuran. After the addition was complete, the reaction mixture was refluxed for 28 hr, 200 ml of dichloromethane was added, and the solution was concentrated. A solution of the residue and 300 ml of dichloromethane was washed with 5% sodium bicarbonate solution and saturated sodium chloride solution. The organic phase was dried, filtered and concentrated. Purification was accomplished by preparative HPLC (Water's Associates Prep LC/System 500, silica gel, eluted with 20:1 dichloromethane/ethyl acetate, flow rate of 200 ml/min, Gow-Mac model 80-800 uv detector). The appropriate fractions were collected, combined and concentrated. The residue solidified during overnight refrigeration (nitrogen atmosphere). The solid was recrystallized from 95% ethanol to give 14.2 g of product, mp 111°–113° C.

ANALYSIS: Calculated for $C_{16}H_{15}ClN_2O_3S$: 54.78%C; 4.31%H; 7.98%N; Found: 54.80%C; 4.24%H; 7.95%N.

EXAMPLE 59

2-(4-Chloro-2-nitrophenyl)-1-(3-methyl-2-thienyl)ethanone

A stirred solution of 6.0 g of 4-chloro-β-(dimethylamino)-α-(3-methyl-2-thienoyl)-2-nitrosty rene, 50 ml of 1,4-dioxane and 10 ml of water was refluxed for 16 hr and allowed to cool. The cooled solution was concentrated, and the residue was partitioned between dichloromethane and water. The organic phase was dried over anhydrous sodium sulfate, filtered and concentrated. A stirred solution of the residue, dioxane and water was refluxed overnight and was worked-up as above. The residue was purified by preparative HPLC (Waters Associates Prep LC/Model 500, silica gel, sample applied in dichloromethane (20 ml), eluted with dichloromethane, 200 ml/min flow rate, Gow Mac Model 80-800 UV detector). The appropriate fractions were concentrated and the residue was recrystallized from 95% ethanol to give 3.03 g of product, mp 105°–107° C.

ANALYSIS: Calculated for $C_{13}H_{10}ClNO_3S$: 52.80%C; 3.41%H; 4.74%N; Found: 52.75%C; 3.46%H; 4.65%N.

EXAMPLE 60

4-Chloro-N-methyl-α-(3-methyl-2-thienyl)-2-nitrobenzeneethanamine hydrochloride To a cooled (−60° C.) solution of 0.06 g of 2-(4-chloro-2-nitrophenyl)-1-(3-methyl-2-thienyl)ethanone in 270 ml of toluene, 70 ml of methyl amine was added under a dry-ice-isopropanol condenser. The mixture was stirred for 0.5 hr. A solution of 4.6 ml of titanium tetrachloride in 46 ml of toluene was added dropwise. The dry-ice-isopropanol condenser was removed, a water condenser was attached, and the reaction was heated at an internal temperature of 75° C. for 2 hrs and stirred overnight at room temperature. The mixture was filtered and the filtrate was evaporated. To a solution of the residue in 250 ml of anhydrous methanol, ethereal hydrogen chloride was added dropwise until a pH of 3–5 was attained. A solution of 1.89 g of sodium cyanoborohydride in 25 ml of anhydrous methanol was added, and the mixture was stirred for 0.5 hr. An additional 1.0 g of sodium cyanoborohydride was added, and the mixture was stirred for one hr. The reaction was kept in the acidic pH range by periodic addition of ethereal hydrogen chloride. The solvent was evaporated, the residue was basified with 10% sodium hydroxide solution and extracted with ether. The combined extracts were washed with water, dried over anhydrous sodium sulfate, and concentrated. Purification was accomplished by preparative HPLC (Waters Associates Prep LC/System 500A, silica gel, 200 ml/min flow rate eluted with ethyl acetate and monitored by a Gow-Mac Model 80-800 uV detector. The appropriate fractions were collected and concentrated, and the residue was dissolved in ether and ethereal-hydrogen chloride was added to afford 5.6 g of product, mp 195°–197° C.

ANALYSIS: Calculated for $C_{14}H_{15}ClN_2O_2S\cdot HCl$: 48.42% C; 4.64%H; 8.07%N; Found: 48.55%C; 4.73%H; 8.08%N.

EXAMPLE 61

2-Amino-4-chloro-N-methyl-α-(3-methyl-2-thienyl)-benzeneethanamine dihydrochloride A solution of 10 g of α-(3-methyl-2-thienyl)-N-methyl-4-chloro-2-nitrobenzeneethana mine in 150 ml of 95% ethanol and 40 ml water was treated with 22 g of reduced electrolytic iron and 1 ml of concentrated hydrochloric acid, and the mixture was refluxed for 0.5 hr, with stirring. The resulting mixture was filtered, and the filter cake was washed with 95% ethanol. The filtrate was basified with 10% sodium hydroxide solution, extracted with dichloromethane and the organic phase was dried over anhydrous sodium sulfate, filtered, and concentrated. Purification of the residue was accomplished by preparative HPLC (Water's Associates Prep LC/System 500A, silica gel, eluted with methanol, flow rate of 200 ml/min, Gow-Mac Model 80-800 UV detector). The appropriate fractions were collected, combined and concentrated. The residue was dissolved in ether, the solution was filtered, and the filtrate was concentrated. The residue was dissolved in methanol, a few drops of ethereal hydrogen chloride was added followed by anhydrous ethyl ether dropwise until a precipitate appeared. The precipitate was collected, and the filter cake was recrystallized from methanol and anhydrous ether to afford 8.4 g of product.

ANALYSIS: Calculated for $C_{14}H_{17}ClN_2S\cdot 2HCl$: 47.54%C; 5.41%H; 7.92%N; Found: 47.51%C; 5.35%H; 7.91%N.

EXAMPLE 62

4-Chloro-β-(dimethylamino)-α-(2-methyl-3-thenoyl)-2-nitrosytrene

To a stirred solution of 12.62 g of trans-β-(dimethylamino)-4-chloro-2-nitrosytrene and 100 ml of tetrahydrofuran was added 6.07 g of triethylamine and a solution of 9.64 g of 2-methyl-3-thenoyl chloride and 20 ml of tetrahydrofuran over 5 mins, under nitrogen. The solution was refluxed 24 hrs. The mixture was evaporated, the residue was dissolved in dichloromethane and washed with 1% sodium bicarbonate (aq) and brine. The organic phase was dried over anhydrous sodium sulfate, filtered, and evaporated. The residue was purified by preparative HPLC (Waters Associates Prep LC/System 500, silica gel, sample loaded in dichloromethane, eluted with 10:1 dichloromethane:ethyl acetate). The appropriate fractions were combined and evaporated to yield 1.75 g of product, mp 142°–144° C.

ANALYSIS: Calculated for $C_{16}H_{15}ClN_2O_3S$: 54.78%C; 4.31%H; 7.98%N; Found: 55.15%C; 4.34%H; 7.88%N.

EXAMPLE 63

2-(4-Chloro-2-nitrophenyl)-1-(2-methyl-2-thienyl)ethanone

A stirred solution of 4.5 g of 4-chloro-β-(dimethylamino-α-(2-methyl-3-thienoyl)-2-nitrostyr ene, 60 ml of 1,4-dioxane and 15 ml of water was refluxed for 48 hrs and then evaporated. Water (20 ml) was added, and the aqueous phase was extracted with dichloromethane. The combined organic phase was dried over anhydrous sodium sulfate and evaporated. The residue was purified by preparative HPLC (Water's Associates Prep LC/Model 500, silica gel, eluted with 5:2 dichloromethane;hexane, Gow Mac model 80-800 uv detector). The appropriate fractions were combined and evaporated to give 2.70 g of product, mp 142°–143° C.

ANALYSIS: Calculated for $C_{13}H_{10}ClNO_3S$: 52.80%C; 3.41%H; 4.74%N; Found: 52.75%C; 3.35%H; 4.68%N.

EXAMPLE 64

4-Chloro-N-methyl-α-(2-methyl-3-thienyl)-2-nitrobenzeneethanamine

To a stirred, chilled (−78° C.) solution of 13.1 g of 2-(4-chloro-2-nitrophenyl)-1-(2-methyl-3-thienyl)ethanone and 175 ml of toluene, was added 18.65 g of methyl amine. The solution was stirred 15 mins, and then a solution of 4.41 g of titanium tetrachloride and 25 ml of toluene was added over 0.5 hr. The solution was stirred at −78° C. for 0.5 hr and allowed to warm to room temperature. The mixture was heated at 80° C. for 5 hr allowed to stand at room temperature overnight. The mixture was filtered and evaporated to yield 13.9 g of an oil.

A solution of the oil and 400 ml of methanol was maintained at pH 3 to 5 while a solution of 5.93 g of sodium cyanoborohydride and 70 ml of methanol was added over 15 mins. The solution was stirred overnight, poured into 200 ml ice, and basified with 10% aqueous sodium hydroxide. The solution was concentrated in vacuo, and the aqueous phase was extracted with dichloromethane. The combined organic phase was dried over anhydrous sodium sulfate, filtered and evaporated. The residue was purified by preparative HPLC (Waters Associates Prep LC/System 500, silica gel, loaded in dichloromethane, eluted with ethyl acetate). The appropriate fractions were combined and evaporated to yield 11.3 g of product, mp 44°–46° C.

ANALYSIS: Calculated for $C_{14}H_{15}ClN_2O_2S$: 54.10%C; 4.86%H; 9.01%N; Found: 54.21%C; 4.94%H; 9.19%N.

EXAMPLE 65

2-Amino-4-chloro-N-methyl-α-(2-methyl-3-thienyl)-benzeneethanamine dihydrochloride A mixture of 5.00 g of α-(2-methyl-3-thienyl)-N-methyl-4-chloro-2-nitrobenzeneethanamine, 9.32 g of iron powder, 100 ml of 95% ethanol, 25 ml of water, and 0.7 ml of concentrated hydrochloric acid was heated at reflux for 1.5 hr. The mixture was filtered through celite, and the organic phase was evaporated. The residue was basified with 10% aqueous sodium hydroxide, and extracted with dichloromethane. The combined organic phase was dried over anhydrous sodium sulfate, filtered and evaporated. The residue was dissolved in methanol and acidified with ethereal hydrogen chloride. The solution was diluted with ether, and the solid was collected, washed with ether, dried in vacuo, and recrystallized from methanol/ether to give 2.6 g of product, mp 242°-243° C. (dec.)

ANALYSIS Calculated for $C_{14}H_{17}ClN_2S \cdot 2HCl$: 47.54%C; 5.41%H; 7.92%N; Found: 47.44%C; 5.26%H; 7.85%N.

EXAMPLE 66

2,2-Dimethyl-N-[2-[2-(3-methyl-2-thienyl)-2-(1-propyl)aminoethyl]phenyl]propanamide To a stirred, chilled (−10° C.) solution of 10.14 g of N-[(2-methyl)-phenyl]-2,2-dimethylpropanamide and 80 ml of tetrahydrofuran, was added over 45 min 48 ml of 2.5M n-butyllithium in hexane, maintaining the temperature below 0° C. The solution was stirred for 2 hr, with cooling. To the suspension, was added a solution of 10.6 g of 3-methyl-2-thiophene carboxaldehyde-n-propylimine and 45 ml of tetrahydrofuran, with stirring and cooling over 15 min. The solution was stirred for 1.5 hr, with cooling, and then 150 ml of water was added. The mixture was concentrated. The residue was extracted with dichloromethane, and the organic phase was dried over anhydrous sodium sulfate, filtered, and concentrated. Purification of the residue was accomplished by Preparative HPLC (Water Associates Prep LC/System 500, silica gel, eluted with ethyl acetate, flow rate 200 ml/min, Gow Mac model 80-800 UV detector). The appropriate fractions were combined and concentrated to give 15.2 g of product, as an oil.

ANALYSIS: Calculated for $C_{21}H_{30}N_2OS$: 70.35%C; 8.43%H; 7.81%N; Found: 70.34%C; 8.37%H; 7.62%N.

EXAMPLE 67

2-Amino-α-(3-methyl-2-thienyl-N-(1-propyl)benzeneethanamine dihydrochloride

To a solution of 6.0 g of N-[2-[2-(1-propylamino)-2-(3-methyl-2-thienyl)ethyl]phenyl]-2,2-dimethylpropanamide, was added 100 ml of 6N hydrochloric acid. The reaction mixture was refluxed, with stirring, for 8 hr, the solution was decanted over 100 g of ice and basified with 30 ml of 50% sodium hydroxide solution. The mixture was extracted with dichloromethane and the organic phase was dried over anhydrous sodium sulfate, filtered, and concentrated. The residue was purified by preparative HPLC (Waters Associates Prep LC/System 500, silica gel, eluted with methanol, flow rate of 200 ml/min, Gow Mac model 80-80 uv detector). The appropriate fractions were collected, combined, and concentrated. The residue was dissolved in 100 ml of diethyl ether and filtered. The filtrate was concentrated. The residue was acidified with ethereal hydrogen chloride in methanol and diluted with diethyl ether to afford 4.12 g of product, mp 196°-198° C.

ANALYSIS Calculated for $C_{16}H_{22}N_2S \cdot 2HCl$: 55.23%C; 6.96%H; 8.07%N; Found: 55.67%C; 6.98%H; 7.96%N.

EXAMPLE 68

2,2-Dimethyl-N-[2-[2-(3-methyl-2-thienyl)-2-(ethyl)aminoethyl][phenyl]propanamide To a stirred, chilled (−10° C.) solution of 8.68 g of N-[(2-methyl)phenyl]-2,2-dimethylpropanamide and 200 ml of tetrahydrofuran, was added dropwise over 1 hr. with stirring, 50 ml of 2.5M of n-butyllithium in hexane, maintaining the temperature below 0° C. The solution was stirred for 1 hr with cooling. To the stirred, cooled suspension, was added over 15 mins, a solution of 8.0 g of 3-methyl-2-thiophenecarboxaldehyde ethylimine in 100 ml of tetrahydrofuran. The solution was stirred for 2 hr (max temp 5° C.) and then quenched with 50 ml of water. The mixture was concentrated. The residue was extracted with dichloromethane and the organic phase was dried over anhydrous sodium sulfate, filtered, and concentrated. The residue was purified by preparative HPLC (Waters Associates Prep LC/System 500 A, silica gel, eluted with ethyl acetate, flow rate of 200 ml/min, Gow Mac Model 80-800 uv detector). The appropriate fractions were combined and concentrated. The residue was dissolved in ether and ethereal-hydrochloric acid was added to give 12.16 g of product, mp 114° C. (dec.).

ANALYSIS: Calculated for $C_{20}H_{28}N_2OS \cdot HCl$: 63.06%C; 7.67%H; 7.35%N; Found: 62.79%C; 7.61%H; 6.96%N.

EXAMPLE 69

2-Amino-N-ethyl-α-(3-methyl-2-thienyl)benzeneethanamine dihydrochloride

A solution of 9.2 g of N-[2-[2-(ethylamino)-2-(3-methyl-2-thienyl)ethyl]phenyl]-2,2-dimethylpropanamide in 160 ml of 6N hydrochloric acid was refluxed for 8 hrs. The solution was decanted over ice and basified with 50% sodium hydroxide solution. The aqueous mixture was extracted with dichloromethane, and the organic phase was dried over anhydrous sodium sulfate, filtered and concentrated. The residue was purified by Preparative HPLC (Water Associates Prep LC/System 500 A, silica gel, eluted with methanol, flow rate of 200 ml/min, Gow-Mac Model 80-800 uv detector). The appropriate fractions were collected and concentrated. The residue was dissolved in ether, filtered, and concentrated. The residue was dissolved in methanol, ethereal-hydrogen chloride was added, and the solution was diluted with anhydrous ether to afford 5.0 g of product, mp 202°-204° C.

ANALYSIS: Calculated for $C_{15}H_{20}N_2S \cdot 2HCl$: 54.05%C; 6.65%H; 8.40%N; Found: 54.56%C; 6.77%H; 8.21%N.

EXAMPLE 70

β-(Dimethylamino)-α-(3-methyl-2-thenoyl)-2-nitrostyrene

To a solution of 43 g of 2-nitrotoluene, and 160 ml of dimethylformamide, was added 110 ml of N,N-dimethylformamide dimethylacetal, with stirring, and the mixture was heated at 128° C., with distillation overnight. The reaction mixture was concentrated to afford 47.2 g of the corresponding enamine. The enamine was dissolved in 350 ml of tetrahydrofuran and 26.82 g of triethylamine and 42.08 g of 3-methyl-2-thienoylchloride was added. After stirring for 0.5 hr, the mixture was refluxed for 5 hr, and stirred at room temperature overnight. The reaction mixture was diluted with 250 ml of dichloromethane and concentrated. The residue was extracted with dichloromethane, and the organic phase was washed with 10% sodium bicarbonate solution, dried over anhydrous sodium sulfate, filtered, and concentrated. The residue was purified by Preparative HPLC (Waters Associates Prep LC/System 500 A, silica gel, eluted with 20:1 dichloromethane/ethyl acetate solution, flow rate of 200 ml/min, GOW MAC model 80-800 UV detector). The appropriate fractions were combined and concentrated. The residue crystallized at room temperature. Recrystallization from 95% ethanol gave 50.6 g of product, mp 101°-103° C.

ANALYSIS: Calculated for $C_{16}H_{16}N_2O_3S$: 60.74%C; 5.10%H; 8.85%N; Found: 60.65%C; 5.74%H; 8.79%N.

EXAMPLE 71

2-(2-Nitrophenyl)-1-(3-methyl-2-thienyl)ethanone

A solution of 62.0 g of β-(dimethylamino)-α-(3-methyl-2-thenoyl)-2-nitrostyrene in 565 ml of 1,4-dioxane and 115 ml of water was refluxed for 48 hr and concentrated. The residue was extracted with dichloromethane, and the organic phase was washed with water, dried over anhydrous sodium sulfate, filtered, and concentrated. The residue crystallized at room temperature. Recrystallization from 95% ethanol gave 34.2 g of product, mp 85°-86.5° C.

ANALYSIS: Calculated for $C_{13}H_{11}NO_3S$: 59.76%C; 4.24%H; 5.36%N; Found: 59.86%C; 4.23%H; 5.36%N.

EXAMPLE 72

1-(3-Methyl-2-thienyl)-2-(2-nitrophenyl)ethanone oxime

A mixture of 22.0 g of 1-(3-methyl-2-thienyl)-2-(2-nitrophenyl)ethanone in 210 ml of 95% ethanol, 11.7 g of hydroxylamine hydrochloride in 28 ml water, and 25.04 g of sodium acetate trihydrate in 28 ml water was refluxed overnight. The mixture was allowed to cool. The precipitate was collected and crystallized from 95% ethanol to give 17.85 g of product, mp 105°-100° C.

ANALYSIS: Calculated for $C_{13}H_{12}N_2O_3S$: 56.51%C; 4.38%H; 10.14%N; Found: 56.49%C; 4.43%H; 10.11%N.

EXAMPLE 73

1-(3-Methyl-2-thienyl)-2-(2-nitrophenyl)ethanone oxime acetate

A mixture of 15.0 g of 1-(3-methyl-2-thienyl)-2-(2-nitrophenyl)ethanone oxime, 27 ml of pyridine and 14 ml of acetic anhydride was heated on a steam bath for 0.5 hr, with stirring. The solution was decanted into ice-water. The solid was collected and recrystallized from 95% ethanol to give 14.8 g of product, mp 60°-68° C.

ANALYSIS: Calculated for $C_{15}H_{14}N_2O_4S$: 56.59%C; 4.43%H; 8.80%N; Found: 56.28%C; 4.30%H; 8.72%N.

EXAMPLE 74

2-Amino-α-(3-methyl-2-thienyl)benzeneethanamine dihydrochloride

To a solution of 7.44 g of 1-(3-methyl-2-thienyl)-2-(2-nitrophenyl)ethanone oxime acetate and 50 ml of tetrahydrofuran maintained at 0° C., was added 233.7 ml of a 1M solution of borane-tetrahydrofuran complex in tetrahydrofuran, with stirring. The solution was stirred at room temp overnight and quenched with 100 ml of 10% aqueous sodium hydroxide solution. The solution was stirred for 15 mins and then concentrated. The aqueous phase was extracted with dichloromethane. The combined organic phase was dried over anhydrous sodium sulfate, filtered, and evaporated. The residue was purified by preparative HPLC (Waters Associates Prep LC/System 500, silica gel, material loaded and eluted with ethyl acetate). The appropriate fractions were combined to yield 1.91 g of 2-nitro-α-(3-methyl-2-thienyl)benzeneethamine.

The benzeneethanamine was combined with material similarly prepared. The mixture (2.95 g), 6.28 g of iron powder, 65 ml of 95% ethanol, 17 ml of water, and 0.47 ml of concentrated hydrochloric acid was heated at reflux for 1.5 hr, with stirring. The mixture was cooled, filtered through Celite, and concentrated in vacuo. The residue was extracted with dichloromethane, and the combined organic phase was dried over anhydrous sodium sulfate, filtered, and concentrated. The residue was dissolved in 20 ml methanol. The solution was acidified with ethereal hydrogen chloride and the mixture was diluted to 500 ml with ether. The precipitate was filtered, washed with ether, and dried in vacuo, and recrystallized from methanol/ether to afford 2.75 g of product, mp 228°-229° C. (dec.).

ANALYSIS: Calculated for $C_{13}H_{16}Cl_2N_2S \cdot 2HCl$: 51.14%C; 5.94%H; 9.18%N; Found: 51.11%C; 5.97%H; 9.05%N.

EXAMPLE 75

2,2-Dimethyl-N-(2-methyl-4-trifluoromethylphenyl)-propanamide

To a chilled (28° C.) solution of 4.91 g of 2,2-dimethyl-N-(4-trifluoromethylphenyl)propanamide and 80 ml tetrahydrofuran, was added over two mins, 18.5 ml of a 2.5M solution of N-butyllithium in hexane, with stirring. The reaction mixture was stirred for two hours at 0° C. and added, dropwise over eight minutes, to a solution of 3.19 g of iodomethane and 7 ml of hexane, keeping the temperature between −2° C.+1° C. The solution was stirred for 45 mins (internal temperature reached 18° C.). Water (20 ml) was added and the mixture was extracted with dichloromethane. The combined organic phase was dried over anhydrous sodium sulfate, filtered, and concentrated. The mixture was separated by preparative HPLC (Waters Associates Prep LC/System 500, silica gel, sample applied in and eluted with methylenechloride, 200 ml/min flow rate). The appropriate fractions were combined, concentrated, and the residue was recrystallized from toluene to give 2.23 g of product, mp 111°-114° C.

ANALYSIS: Calculated for $C_{13}H_{16}F_3NO$: 60.22%C; 6.22%H; 5.40%N; Found: 60.44%C; 6.29%H; 5.41%N.

EXAMPLE 76

2,2-Dimethyl-N-[2-[2-methylamino-2-(3-methyl-2-thienyl)ethyl]-4-trifluoromethylphenyl]propanamide To a chilled (10° C.) solution of 12.81 g of 2,2-dimethyl-N-(2-methyl-4-trifluoromethylphenyl)propanamide and 200 ml of anhydrous tetrahydrofuran, was added dropwise over 20 min, 48 ml of a 2.5M solution of n-butyllithium in hexanes, with stirring. The solution was stirred, with cooling, for 1 hr, and 10.65 g of an 85% solution of 3-methyl-2-thiophenecarboxaldehyde methylimine in toluene, and 20 ml of tetrahydrofuran was added, dropwise over 10 min, with stirring. After stirring and cooling for 1.5 hr, 60 ml of water was added, and the mixture was evaporated. The residue was diluted with water and extracted with dichloromethane. The combined, organic phase was dried over anhydrous sodium sulfate, filtered, and concentrated. The residue was separated by HPLC (Waters Associates Prep LC/System 500, silica gel, 200 ml/min flow rate; the residue was dissolved in sufficient ethyl acetate-hexane (1:1) to give 50 ml of solution, and the solution was applied in 25 ml portions to the columns, Gow Mac UV detector). The appropriate fractions were combined and concentrated. The residue was purified again by preparative HPLC under similar conditions, and finally, using a single recycle (elution with ethyl acetate-hexane (1:1)) to afford 9.53 g of product, mp 64°–69° C.

ANALYSIS: Calculated for $C_{20}H_{25}F_3N_2OS$: 60.28%C; 6.32%H; 7.03%N; Found: 60.25%C; 6.25%H; 6.88%N.

EXAMPLE 77

2-Amino-N-methyl-α-(3-methyl-2-thienyl)-5-trifluoromethylbenzeneethanamine dihydrochloride A solution of 8.29 g of 2,2-dimethyl-N-[2-[2-methylamino-2-(3-methyl-2-thienyl)ethyl]-4-trifluoromethylphenyl]propanamide and 250 ml of 6N hydrochloric acid was refluxed for 10 hr, with stirring. The cooled solution was decanted over crushed ice and water, basified with 50% sodium hydroxide solution, and extracted with dichloromethane. The combined organic phase was washed with saturated brine, dried over anhydrous sodium sulfate, filtered, and concentrated. The residue was separated by preparative HPLC (Waters Associates Prep LC/System 500, silica gel, sample applied in and eluted with methanol, 200 ml/min flow rate). The appropriate fractions were combined and evaporated. The residue was dissolved in ether and allowed to stand for 1 hr. The solution was filtered and the filtrate concentrated. The residue crystallized during refrigerated storage. A solution of the residue and ~5 ml methanol was treated with excess ethereal hydrogen chloride, and the solution was gradually diluted with ether. The precipitate was collected, washed with ether, and dried in vacuo at 40° C. over sodium hydroxide pellets to give 0.29 g of product, mp 209°–212° C. (dec.).

ANALYSIS: Calculated for $C_{15}H_{17}F_3N_2S \cdot 2HCl$: 46.52%C; 4.94%H; 7.23%N; Found: 46.44%C; 4.90%H; 7.22%N.

EXAMPLE 78

2-Amino-5-bromo-N,N-dimethyl-α-(3-methyl-2-thienyl)benzeneethanamine

To a solution of 6.0 g of 2-amino-N,N-dimethyl-α-(3-methyl-2-thienyl)benzeneethanamine in 30 ml of dimethylformamide, was added 5.32 g of N-bromosuccinimide in 30 ml of dimethylformamide, with stirring, and the mixture was stirred overnight at room temperature. The solution was concentrated, basified with 10% sodium hydroxide solution, and extracted with dichloromethane. The organic phase was dried over anhydrous sodium sulfate, filtered, and concentrated. The residue was purified by preparative HPLC (Water's Associates Prep LC/System 500a, silica gel, eluted with methanol, flow rate of 200 ml/min, Gow Mac model 80–800 UV detector). The appropriate fractions were collected and concentrated. The residue was dissolved in 100 ml of diethylether and filtered. The filtrate was concentrated. The residue was triturated in hexane to give 2.2 g of product, mp 96°–98° C.

ANALYSIS: Calculated for $C_{15}H_{19}BrN_2S$: 53.10%C; 5.64%H; 8.26%N; Found: 52.82%C; 5.66%H; 8.15%N.

EXAMPLE 79

β-(Dimethylamino)-α-(3-methyl-2-thenoyl)-2-nitro-4-trifluoromethylstyrene

A stirred solution of 98.68 g of 4-trifluoromethyl-2-nitrotoluene in 240 ml of dimethylformamide and 73.0 g of 94% dimethylformamide dimethylacetal was heated to 128° C. and stirred overnight, with distillation. Concentration gave 115 g of the corresponding enamine, as an oil, which solidified on storage under refrigeration (nitrogen atmosphere).

To a solution of 115 g of the enamine, obtained above, in 550 ml of tetrahydrofuran and 66 ml of triethylamine, was added dropwise, 75.8 g of 3-methyl-2-thiophenecarbonylchloride in 170 ml of tetrahydrofuran. After the addition was complete, the solution was refluxed for 77 hr. Dichloromethane (200 ml) was added, and the solution was concentrated. A solution of the residue and 900 ml of dichloromethane was washed with 5% sodium bicarbonate solution (which was diluted with 400 ml water), and saturated sodium chloride solution. The organic phase was dried over anhydrous sodium sulfate, filtered, and concentrated. The residue solidified at room temperature. Purification of the solid was accomplished by preparative HPLC (Waters Associates Prep LC/System 500, silica gel, eluted with 20:1 dichloromethane/ethyl acetate, flow rate of 200 ml/min, GOW-MAC model 80-800 uv detector). The appropriate fractions were collected, combined, and concentrated. The residue solidified at room temperature. The solid was recrystallized from 95% ethanol to give 70.2 g of product, mp 118°–118.5° C.

ANALYSIS: Calculated for $C_{17}H_{15}F_3N_2O_3S$: 53.12%C; 3.93%H; 7.29%N; Found: 52.79%C; 3.91%H; 7.21%N.

EXAMPLE 80

2-(4-Trifluoromethyl-2-nitrophenyl)-1-(3-methyl-2-thienyl)ethanone

A stirred solution of 6.4 g of 4-trifluoromethyl-β-(dimethylamino)-α-(3-methyl-2-thienoyl)-2-nitrostyrene, 49 ml of 1,4-dioxane, and 10 ml of water was refluxed for 42 hr. The cooled solution was concentrated, and the residue was partitioned between dichloromethane and water. The organic phase was dried over anhydrous sodium sulfate, filtered, and concentrated. The residue crystallized upon standing at room temperature. The solid was recrystallized from 95% ethanol to afford 1.9 g (35%) of product, mp 120°–122° C.

ANALYSIS: Calculated for $C_{14}H_{10}F_3NO_3S$: 51.06%C; 3.06%H; 4.25%N; Found: 51.12%C; 2.96%H; 4.10%N.

EXAMPLE 81

2-Amino-N-methyl-α-(3-methyl-2-thienyl)-4-trifluoromethylbenzeneethanamine 2-(4-Trifluoromethyl-2-nitrophenyl)-1-(3-methyl-2-thienyl)ethanone was converted to the methyl imine and was reduced to the methyl amine using sodium cyanoborohydride as described for the preparation of 4-chloro-α-(2-methyl-3-thienyl)-N-methyl-4-chloro-2-nitrobenzeneethanamine (EXAMPLE 64).

A mixture of 3.3 g of α-(3-methyl-2-thienyl)-N-methyl-2-nitro-4-trifluoromethylbenzeneethanamine hydrochloride, 4.8 g of iron powder, 13 ml of water, 50 ml of 95% ethanol, and concentrated 350 μl hydrochloric acid was refluxed for 1.5 hrs. The mixture was filtered through Celite, the filter cake washed with water, and the organic phase of the filtrate was concentrated in vacuo. The residue was diluted with 50 ml of water and basified with 10% (aq) sodium hydroxide solution. The aqueous phase was extracted with dichloromethane, and the combined organic phase was dried over anhydrous sodium sulfate and concentrated. The residue was triturated with hexane to afford 2.1 g of product, mp 52°–54° C.

ANALYSIS: Calculated for $C_{15}H_{17}F_3N_2S$: 57.31%C; 5.45%H; 8.91%N; Found: 57.11%C; 5.42%H; 8.89%N.

EXAMPLE 82

N-Formyl-2-methoxy-N-methyl-α-(3-methyl-2-thienyl)benzeneethanamine

To an ice-water chilled solution of 5.10 g of N-formyl-2-hydroxy-N-methyl-α-(3-methyl-2-thienyl)benzeneethanamine and 100 ml of tetrahydrofuran, was added 2.24 g of potassium t-butoxide and then a solution of 2.52 g of dimethylsulfate and 25 ml of tetrahydrofuran dropwise, with stirring. The mixture was stirred at ice-bath temperature for 30 min, at room temperature for one hr, and at reflux for 30 mins. Additional dimethylsulfate and potassium t-butoxide were added and the mixture was refluxed for 20 min. The reaction mixture was decanted into 40 ml of water and basified with 10% sodium hydroxide solution. The mixture was extracted with dichloromethane. The combined organic phase was dried over anhydrous sodium sulfate, filtered and concentrated. The residue was combined with a previous sample. The combined residue was purified by preparative HPLC (Water Associates Prep LC/System 500, silica gel, material applied as a solution in dichloromethane, eluted with ethyl acetate-hexane (1:1, 200 ml/min flow rate). The appropriate fractions were combined and concentrated. The residue crystallized during refrigerated storage. Recrystallization from cyclohexane afforded 3.5 g of the product, mp 80°–83° C.

ANALYSIS: Calculated for $C_{16}H_{19}NO_2S$: 66.41%C; 6.62%H; 4.84%N; Found: 66.10%C; 6.61%H; 4.88%N.

EXAMPLE 83

2-Methoxy-N-methyl-α-(3-methyl-2-thienyl)benzeneethanamine hydrochloride

A solution of 1.83 g of N-formyl-2-methoxy-N-methyl-α-(3-methyl-2-thienyl)benzeneethanamine, 25 ml of methanol, and 25 ml of 3N hydrochloric acid solution was heated for 3 hr under reflux. Methanol was added to clear the solution. The solution was concentrated, the residue was diluted with water, and extracted with ether. The aqueous phase was basified with 2.5N sodium hydroxide solution and extracted with dichloromethane. The combined organic phase was dried over anhydrous sodium sulfate, filtered, and concentrated. An ether solution of the residue was treated with excess ethereal hydrogen chloride. Recrystallization from acetonitrile gave 0.83 g of product, mp 201°–203.5° C.

ANALYSIS: Calculated for $C_{15}H_{19}NOS \cdot HCl$: 60.49%C; 6.77%H; 4.70%N; Found: 60.52%C; 6.89%H; 4.78%N.

EXAMPLE 84

2-Dimethylamino-N-formyl-N-methyl-α-(3-methyl-2-thienyl)benzeneethanamine

A solution of 5.0 g of 2-amino-N-formyl-N-methyl-α-(3-methyl-2-thienyl)benzeneethanamine in 48 ml of acetonitrile was treated with 6.5 ml of a 37% formaldehyde solution and 1.9 g of sodium cyanoborohydride. The mixture was stirred for 1.5 hr and then concentrated. The residue was dissolved in 75 ml of ether and washed with 1N potassium hydroxide solution and with saturated brine. The ether solution was dried over anhydrous potassium carbonate and concentrated. The residue was purified by Preparative HPLC (Waters Associates Prep LC/System 500, silica gel, eluted with ethyl acetate, 200 ml/min, Glo-Mac Model 80-800 UV detector). The appropriate fractions were collected and concentrated to give 3.8 g of product, as an oil.

ANALYSIS: Calculated for $C_{17}H_{22}N_2OS$: 67.52%C; 7.33%H; 9.26%N; Found: 67.33%C; 7.34%H; 9.33%N.

EXAMPLE 85

2-Amino-N-methyl-N-(2-methylpropionyl)-α-(3-methyl-2-thienyl)benzeneethanamine

A solution of 5.86 g of 2-amino-N-methyl-α-(3-methyl-2-thienyl)benzeneethanamine and 19.56 g of trimethylorthisobutyrate and 7.94 ml of glacial acetic acid was refluxed 8 hrs, under a nitrogen atmosphere. The reaction mixture was concentrated. The residue was acidified with 10% hydrochloric acid and extracted with ether. The acidic aqueous phase was basified with 10% sodium hydroxide solution and extracted with dichloromethane. The dichloromethane phase was dried over anhydrous sodium sulfate, filtered, and concentrated. The residue was purified by HPLC (Waters Associates Prep LC/Systems 500A, silica gel, eluted with methanol 2% triethylamine/methanol; 200 ml/min flow rate). The appropriate fractions were combined and concentrated, and the residue was crystallized from ethyl acetate to afford 2.33 g of product, mp 137°–141° C.

ANALYSIS: Calculated for $C_{18}H_{24}N_2OS$: 68.31%C; 7.64%H; 8.85%N; Found: 68.27%C; 7.80%H; 8.60%N.

EXAMPLE 86

2-Amino-N-acetyl-N-methyl-α-(5-methyl-2-thienyl)-benzeneethanamine

Thin layer analysis of the crude reaction product of Example 39 (silica gel, 2% triethylamine in methanol) indicated a two component mixture. Purification was accomplished by Preparative HPLC (Waters Associates Prep LC/System 500, silica gel, eluted with 2% triethylamine in methanol, flow rate of 200 ml/min, Gow Mac Model 80-800 UV detector). The fractions containing the faster moving material were combined and concentrated. The residue was dissolved in ether and filtered. The filtrate was concentrated to afford 2.12 g of product, mp 144°–145° C., after drying at 40° C.

ANALYSIS: Calculated for $C_{16}H_{20}N_2OS$: 66.63%C; 6.99%H; 9.71%N; Found: 66.57%C; 7.04%H; 9.52%N.

Reaction Scheme A
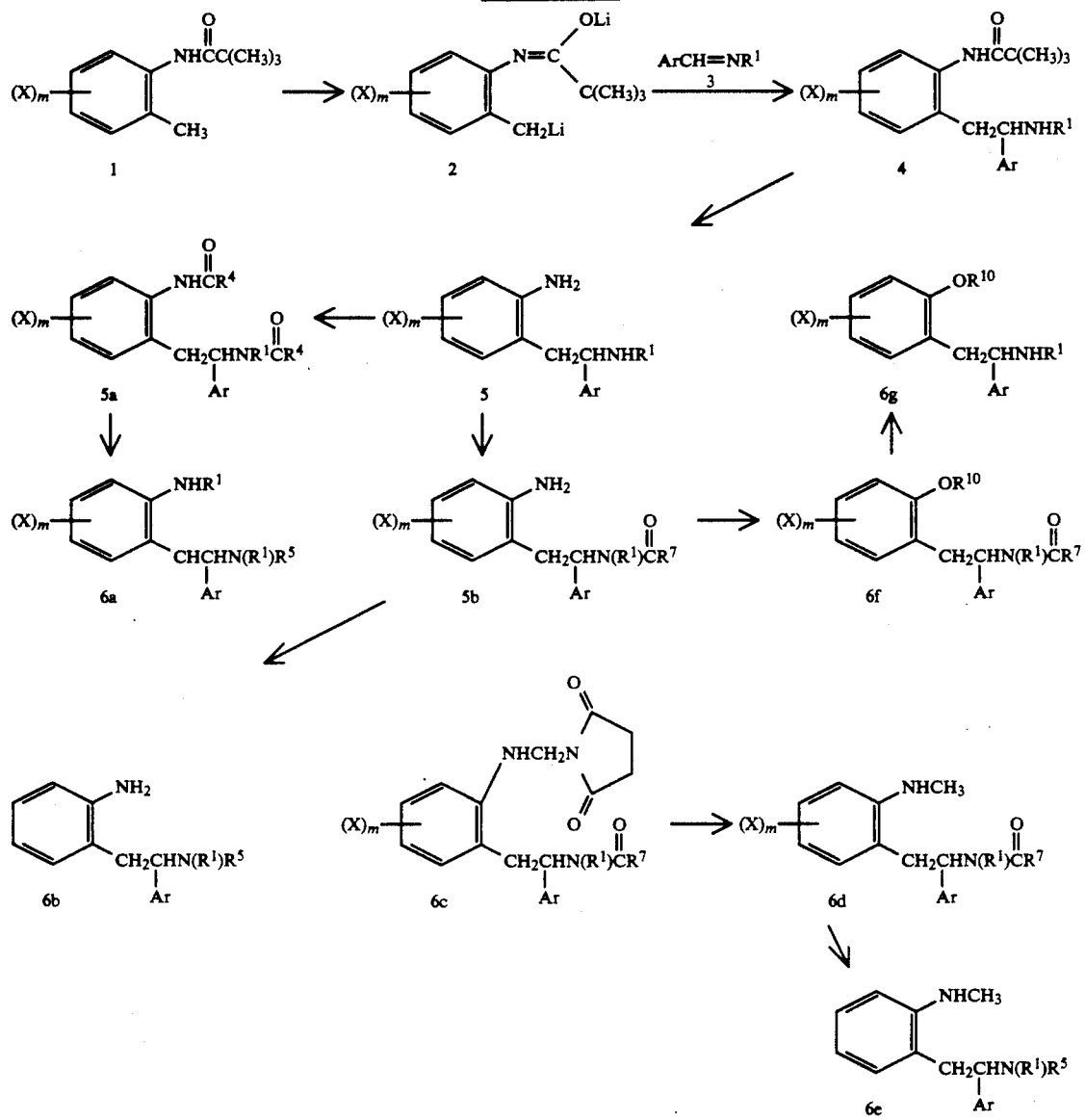
Wherein Ar, X, $R^4$, $R^7$, $R^{10}$, and m are as herein described, $R^1$ is loweralkyl or aralkyl and $R^5$ is hydrogen or loweralkyl.
Reaction Scheme B
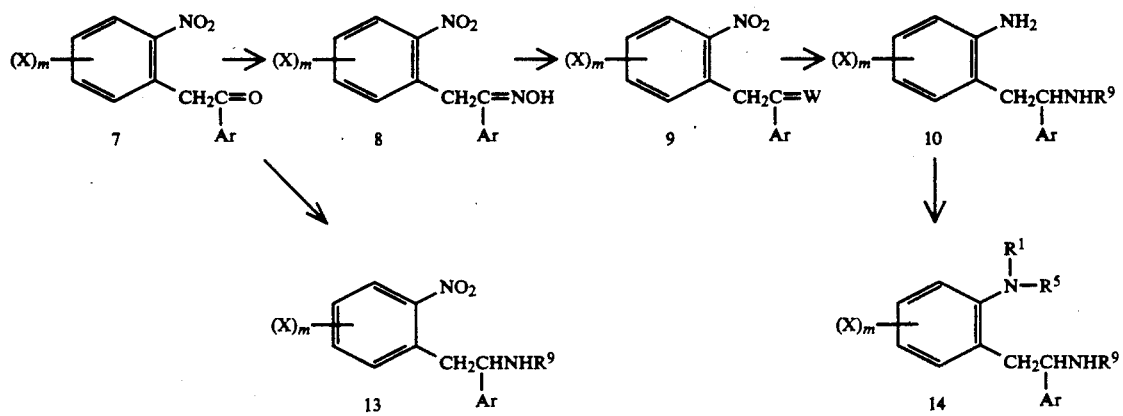

Wherein $R^1$, $R^9$, Ar, X, and m are as herein described; and W is $NOR^8$ wherein $R^8$ is an alkanoyl of from 1 to 5 carbon atoms or $NR^9$ wherein $R^9$ is hydrogen or alkyl of from 1 to 5 carbon atoms.

Reaction Scheme C

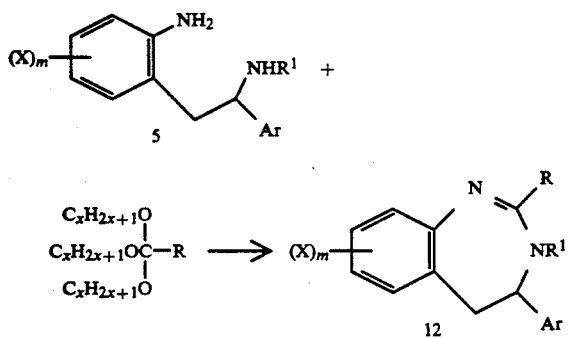

Wherein X, Ar, R and m are previously described; $R^1$ is hydrogen, loweralkyl or aryl; and x is an integer having a value of 1 or 2.

What is claimed is:

1. A compound of the formula:

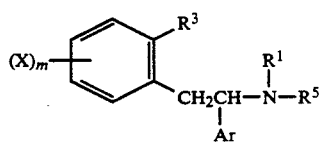

wherein Ar is selected from the group consisting of

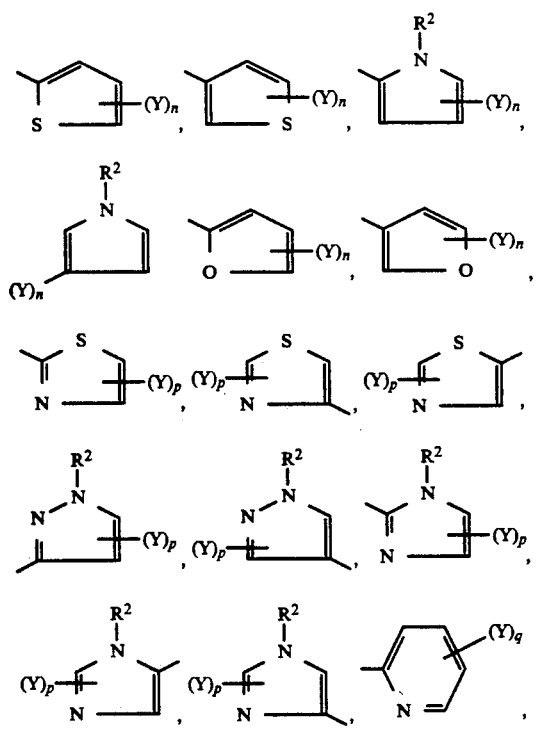

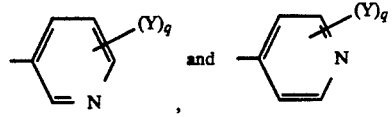

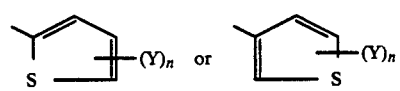

wherein $R^2$ is hydrogen, loweralkyl or loweralkanoyl, Y is selected from the group consisting of halogen, hydroxyl, loweralkyl, loweralkoxy and trifluoromethyl, n is an integer having a value from 0 to 3 inclusive, p is an integer having a value of 0 or 1, and q is an integer having a value from 0 to 4 inclusive; X is selected from the group consisting of halogen, hydroxyl, nitro, loweralkyl, loweralkoxy, and trifluoromethyl; m is an integer having a value from 0 to 3 inclusive; $R^1$ is selected from the group consisting of hydrogen, loweralkyl, and aralkyl; $R^3$ is hydroxy, loweralkoxy, amino, loweralkylamino, diloweralkylamino, nitro, or $NR^6C(O)R^4$ wherein $R^4$ and $R^6$ are independently hydrogen or loweralkyl; and $R^5$ is hydrogen, loweralkyl or $C(O)R^7$ where $R^7$ is hydrogen or loweralkyl; wherein for each value of m, n, p or q each X or Y may be the same or different; the geometrical isomers, optical antipodes or pharmaceutically acceptable acid addition salts thereof.

2. A compound as defined in claim 1 wherein Ar is

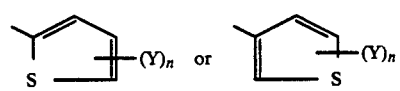

wherein Y is loweralkyl and n is an integer having a value of 0 or 1.

3. The compound of claim 2 wherein $R^3$ is amino.
4. The compound of claim 2 which is 2-amino-N-methyl-α-(3-thienyl)benzeneethanamine.
5. The compound of claim 2 which is 2-amino-N-methyl-α-(3-methyl-2-thienyl)benzeneethanamine.
6. The compound of claim 2 which is 2-amino-N-methyl-α-(2-thienyl)benzeneethanamine.
7. The compound of claim 2 which is 2-amino-5-bromo-N-methyl-α-(3-methyl-2-thienyl)benzeneethanamine.
8. The compound of claim 2 which is 2-amino-3,5-dibromo-N-methyl-α-(3-methyl-2-thienyl)benzeneethanamine.
9. The compound of claim 2 which is 2-amino-N-methyl-α-(5-methyl-2-thienyl)benzeneethanamine.
10. The compound of claim 2 which is 2-amino-N-formyl-N-methyl-α-(4-methyl-2-thienyl) benzeneethanamine.
11. The compound of claim 2 which is 2-amino-5-chloro-N-methyl-α-(3-methyl-2-thienyl)benzeneethanamine.
12. The compound of claim 2 which is 2-amino-N-methyl-α-(2-methyl-3-thienyl)benzeneethanamine.
13. The compound of claim 2 which is 2-amino-N-formyl-N-methyl-α-(3-methyl-2-thienyl)benzeneethanamine.

14. The compound of claim 2 which is 2-amino-N,N-dimethyl-α-(3-methyl-2-thienyl)benzeneethanamine.

15. The compound of claim 2 which is N-[2-[2-(N-formyl-N-methyl)amino-2-(3-methyl-2-thienyl)ethyl]phenyl]formamide.

16. The compound of claim 2 which is 2-amino-5-bromo-N-methyl-α-(2-methyl-3-thienyl)benzeneethanamine.

17. The compound of claim 2 which is N-acetyl-2-amino-N-methyl-α-(3-methyl-2-thienyl)benzeneethanamine.

18. A compound as defined in claim 1 wherein $R^3$ is loweralkylamino.

19. A compound of claim 18 which is N-formyl-N-methyl-2-methylamino-α-(3-methyl-2-thienyl)benzeneethanamine.

20. The compound of claim 18 which is N-methyl-2-methylamino-α-(3-methyl-2-thienyl)benzeneethanamine.

21. The compound of claim 18 which is N,N-dimethyl-2-methylamino-α-(3-methyl-2-thienyl)benzeneethanamine.

22. The compound as defined in claim 1 wherein $R^3$ is diloweralkylamino.

23. The compound of claim 22 which is N,N-dimethyl-2-dimethylamino-α-(3-methyl-3-thienyl)benzeneethanamine.

24. A compound as defined in claim 1 wherein $R^3$ is —NHC(O)$R^4$.

25. The compound of claim 24 which is N-[2-[2-methylamino-2-(2-thienyl)ethyl]phenyl]-2,2-dimethylpropanamide.

26. The compound of claim 24 which is N-[2-[2-(methylamino)-2-(3-thienyl)ethyl]phenyl]-2,2-dimethylpropanamide.

27. The compound of claim 24 which is N-[2-[2-methylamino)2-(3-methyl-2-thienyl)ethyl]phenyl]-2,2-dimethylpropanamide.

28. The compound of claim 24 which is N-[2-[2-(methylamino)-2-(2-methyl-3-thienyl)ethyl]phenyl]-2,2-dimethylpropanamide.

29. A compound as defined in claim 1 wherein $R^3$ is hydroxyl.

30. The compound of claim 29 which is N-formyl-2-hydroxy-N-methyl-α-(3-methyl-2-thienyl)benzeneethanamine.

31. The compound of claim 29 which is 2-hydroxy-N-methyl-α-(3-methyl-2-thienyl)benzeneethanamine.

32. A compound as defined in claim 1 wherein Ar is selected from the group consisting of

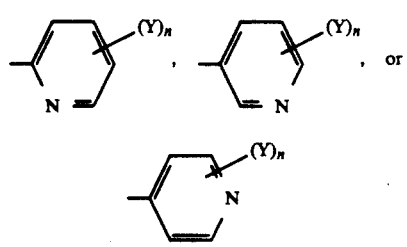

wherein Y is loweralkyl and n is an integer having a value of 0 or 1.

33. The compound of claim 32 wherein $R^3$ is amino.

34. The compound of claim 33 which is 2-amino-N-methyl-α-(2-pyridinyl)benzeneethanamine.

35. The compound of claim 33 which is 2-amino-N-methyl-α-(4-pyridinyl)benzeneethanamine.

36. The compound of claim 33 which is N-acetyl-2-amino-N-methyl-α-(2-pyridinyl)benzeneethanamine.

37. The compound of claim 33 which is 2-amino-N-methyl-α-(3-pyridinyl)benzeneethanamine.

38. The compound of claim 32 wherein $R^3$ is NHC(O)$R^4$.

39. The compound of claim 38 which is N-[2-[2-(methylamino)-2-(3-pyridinyl)ethyl]phenyl]-2,2-dimethylpropanamide.

40. The compound of claim 38 which is N-[2-[2-(methylamino-2-(2-pyridinyl)ethyl]phenyl]-2,2-dimethylpropanamide.

41. The compound of claim 38 which is N-[2-[2-(N-acetyl-N-methyl)amino-2-(2-pyridinyl)]ethyl]phenyl]acetamide.

42. The compound of claim 38 which is N-[2-[2-methylamino)-2-(4-pyridinyl)ethyl]phenyl]-2,2-dimethylpropanamide.

43. A compound as defined in claim 1 wherein Ar is

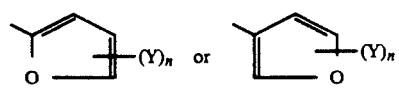

44. A compound of the formula:

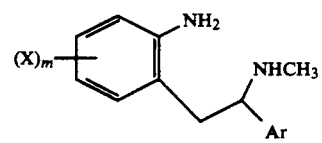

wherein X is halogen, m is zero or 1, and Ar is

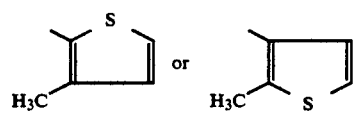

45. A compound as defined in claim 44 wherein X is bromine or chlorine.

46. A pharmaceutical composition comprising an effective convulsion inhibiting amount of a compound as defined in claim 1 and a suitable carrier therefor.

47. A method of inhibiting convulsions comprising administering to a mammal in need of convulsion inhibition a convulsion inhibiting effective amount of a compound as defined in claim 1.

48. The compound of claim 45 which is 2-amino-4-chloro-N-methyl-α-(3-methyl-2-thienyl)benzeneethanamine.

49. The compound of claim 45 which is 2-amino-4-chloro-N-methyl-α-(2-methyl-3-thienyl)benzeneethanamine.

50. The compound of claim 3 which is 2-amino-α-(3-methyl-2-thienyl)-N-(1-propyl)benzeneethanamine.

51. The compound of claim 3 which is 2-amino-N-ethyl-α-(3-methyl-2-thienyl)benzeneethanamine.

52. The compound of claim 3 which is 2-amino-α-(3-methyl-2-thienyl)benzeneethanamine.

53. The compound of claim 3 which is 2-amino-N-methyl-α-(3-methyl-2-thienyl)-5-trifluoromethylbenzeneethanamine.

54. The compound of claim 3 which is 2-amino-5-bromo-N,N-dimethyl-α-(3-methyl-2-thienyl)benzeneethanamine.

55. The compound of claim 3 which is 2-amino-N-methyl-α-(3-methyl-2-thienyl)-4-trifluoromethylbenzeneethanamine.

56. The compound of claim 2 wherein $R^3$ is nitro.

57. The compound of claim 56 which is 4-chloro-N-methyl-α-(3-methyl-2-thienyl)-2-nitrobenzeneethanamine.

58. The compound of claim 56 which is 4-chloro-N-methyl-α-(2-methyl-3-thienyl)-2-nitrobenzeneethanamine.

59. The compound of claim 58 which is α-(3-methyl-2-thienyl)-N-methyl-2-nitro-4-trifluoromethylbenzeneethanamine.

60. The compound of claim 56 which is 2-nitro-α-(3-methyl-2-thienyl)benzeneethanamine.

61. The compound of claim 24 which is 2,2-dimethyl-N-[2-[2-(3-methyl-2-thienyl)-2-(ethyl)aminoethyl]-phenyl]propanamide.

62. The compound of claim 24 which is 2,2-dimethyl-N-[2-[2-(3-methyl-2-thienyl)-2-(2-propyl)aminoethyl]-phenyl]propanamide.

63. The compound of claim 24 which is 2,2-dimethyl-N-[2-[2-methylamino-2-(3-methyl-2-thienyl)ethyl]-4-trifluoromethylphenyl]propanamide.

64. A compound as defined in claim 1 wherein $R^3$ is [hydroxy]loweralkoxy.

65. The compound of claim 64 which is N-formyl-2-methoxy-N-methyl-α-(2-methyl-2-thienyl)benzeneethanamine.

66. The compound of claim 64 which is 2-methoxy-N-methyl-α-(3-methyl-2-thienyl)benzeneethanamine.

67. The compound of claim 2 which is 2-amino-N-methyl-N-(2-methylpropionyl)-α-(3-methyl-2-thienyl)-benzeneethanamine.

68. The compound of claim 2 which is 2-amino-N-acetyl-N-methyl-2-(5methyl-2-[thienyl]thienyl benzeneethanamine 2-amino-N-acetyl-N-methyl-α-(5-methyl-2-thieneyl)benzeneethanamine.

69. A compound as defined in claim 1 wherein $R^3$ is diloweralkylamino.

70. The compound of claim 69 which is 2-dimethylamino-N-formyl-N-methyl-α-(3-methyl-2-thienyl)-benzeneethanamine.

71. A method of treating anxiety of mammals which comprises administering to a mammal in need of anxiety treatment an anxiety treating amount of a compound or a pharmaceutically acceptable acid addition salt thereof of a compound as defined in claim 1.

72. An anxiety treating composition which comprises an anxiety treating effective amount of a compound or a pharmaceutically acceptable acid addition salt thereof of a compound as defined in claim 1 and a pharmaceutically acceptable carrier therefor.

* * * * *